United States Patent
West et al.

(10) Patent No.: US 10,501,723 B2
(45) Date of Patent: Dec. 10, 2019

(54) METHODS OF REPROGRAMMING ANIMAL SOMATIC CELLS

(71) Applicant: Astellas Institute for Regenerative Medicine, Marlborough, MA (US)

(72) Inventors: Michael D. West, Mill Valley, CA (US); Karen B. Chapman, Mill Valley, CA (US); Roy Geoffrey Sargent, San Lorenzo, CA (US)

(73) Assignee: Astellas Institute for Regenerative Medicine, Marlborough, MA (US)

( * ) Notice: Subject to any disclaimer, the term of this patent is extended or adjusted under 35 U.S.C. 154(b) by 0 days.

(21) Appl. No.: 14/525,378

(22) Filed: Oct. 28, 2014

(65) Prior Publication Data
US 2015/0232808 A1 Aug. 20, 2015
US 2017/0152475 A9 Jun. 1, 2017

Related U.S. Application Data

(63) Continuation of application No. 11/989,988, filed as application No. PCT/US2006/030632 on Aug. 3, 2006, now abandoned.

(60) Provisional application No. 60/818,813, filed on Jul. 5, 2006, provisional application No. 60/729,173, filed on Oct. 20, 2005, provisional application No. 60/705,625, filed on Aug. 3, 2005.

(51) Int. Cl.
| | |
|---|---|
| *C12N 5/16* | (2006.01) |
| *C12N 5/0735* | (2010.01) |
| *A01K 67/027* | (2006.01) |
| *C12N 5/071* | (2010.01) |
| *C12N 15/873* | (2010.01) |
| *C12Q 1/6881* | (2018.01) |

(52) U.S. Cl.
CPC ........ *C12N 5/0606* (2013.01); *A01K 67/0271* (2013.01); *C12N 5/0676* (2013.01); *C12N 5/16* (2013.01); *C12N 15/873* (2013.01); *C12Q 1/6881* (2013.01); *C12N 2501/602* (2013.01); *C12N 2501/603* (2013.01); *C12N 2501/605* (2013.01); *C12N 2501/606* (2013.01); *C12N 2501/72* (2013.01); *C12N 2506/00* (2013.01); *C12N 2506/11* (2013.01); *C12Q 2600/158* (2013.01)

(58) Field of Classification Search
CPC ............ C12N 5/0606; C12N 2501/602; C12N 2501/603; C12N 2501/605; C12N 2501/606; C12N 2501/72; C12Q 1/6881; C12Q 2600/158
See application file for complete search history.

(56) References Cited

U.S. PATENT DOCUMENTS

| | | | |
|---|---|---|---|
| 5,166,317 | A | 11/1992 | Wallace |
| 5,480,772 | A | 1/1996 | Wangh |
| 5,651,992 | A | 7/1997 | Wangh |
| 5,830,651 | A | 11/1998 | Cauley |
| 6,011,197 | A | 1/2000 | Strelchenko |
| 6,303,576 | B1 | 10/2001 | Blaschuk et al. |
| 8,048,999 | B2 | 11/2011 | Yamanaka et al. |
| 8,058,065 | B2 | 11/2011 | Yamanaka et al. |
| 8,129,187 | B2 | 3/2012 | Yamanaka et al. |
| 8,278,104 | B2 | 10/2012 | Yamanaka et al. |
| 8,927,279 | B2 | 1/2015 | Jaenisch et al. |
| 2001/0012513 | A1 | 8/2001 | Robl |
| 2002/0001842 | A1 | 1/2002 | Chapman |
| 2002/0090722 | A1 | 7/2002 | Dominko et al. |
| 2002/0142397 | A1 | 10/2002 | Collas |
| 2003/0044976 | A1 | 3/2003 | Dominko |
| 2003/0046722 | A1 | 3/2003 | Collas |
| 2003/0229908 | A1 | 12/2003 | Cibelli et al. |
| 2003/0232430 | A1 | 12/2003 | Cibelli et al. |
| 2005/0014258 | A1 | 1/2005 | Collas |
| 2005/0273870 | A1 | 12/2005 | Robl et al. |
| 2006/0051332 | A1 | 3/2006 | Lanza |
| 2008/0076176 | A1 | 3/2008 | Dominko |
| 2009/0047263 | A1 | 2/2009 | Yamanaka et al. |
| 2009/0227032 | A1 | 9/2009 | Yamanaka et al. |
| 2009/0246875 | A1 | 10/2009 | Yamanaka et al. |
| 2009/0271335 | A1 | 10/2009 | West et al. |

(Continued)

FOREIGN PATENT DOCUMENTS

| | | |
|---|---|---|
| EP | 1 391 503 A1 | 2/2004 |
| EP | 1970446 A1 | 9/2008 |

(Continued)

OTHER PUBLICATIONS

Munsie et al., Current Biology, 10(16): 989-992, 2000, including supplemental materials.*
Cauffman et al., Mol. Human Reproduction, 11(3): 173-181, 2005.*
Pan et al., Biology of Reproduction, 85: 409-416, 2011.*
Yamada-Fukunaga et al., Reproductive Biology and Endocrinology, 11:108, (pp. 1-11), 2013.*
Flemr et al., Biology of Reproduction, 90(6): 1-6, 2014.*
Betts et al., PNAS, 98(3): 1077-1082, 2001.*
Suh et al., Developmental Biology, 270: 488-498, 2004.*
Kim et al., Cell Stem Cell, 4: 472-476, 2009, including Supplemental Data, pp. 1-18.*

(Continued)

*Primary Examiner* — Thaian N Ton
(74) *Attorney, Agent, or Firm* — Wolf, Greenfield & Sacks, P.C.

(57) ABSTRACT

This invention generally relates to methods to obtain mammalian cells and tissues with patterns of gene expression similar to that of a developing mammalian embryo or fetus, and the use of such cells and tissues in the treatment of human disease and age-related conditions. More particularly, the invention relates to methods for identifying, expanding in culture, and formulating mammalian pluripotent stem cells and differentiated cells that differ from cells in the adult human in their pattern of gene expression, and therefore offer unique characteristics that provide novel therapeutic strategies in the treatment of degenerative disease.

10 Claims, 2 Drawing Sheets

(56) References Cited

U.S. PATENT DOCUMENTS

| | | |
|---|---|---|
| 2010/0062533 A1 | 3/2010 | Yamanaka |
| 2010/0167404 A1 | 7/2010 | West et al. |
| 2010/0210014 A1 | 8/2010 | Yamanaka |
| 2010/0216236 A1 | 8/2010 | Yamanaka |
| 2010/0279404 A1 | 11/2010 | Yamanaka et al. |
| 2011/0110899 A1 | 5/2011 | Shi et al. |
| 2011/0143441 A1 | 6/2011 | West et al. |
| 2011/0190730 A1 | 8/2011 | Kirkland et al. |
| 2011/0223669 A1 | 9/2011 | Yamanaka et al. |
| 2011/0250692 A1 | 10/2011 | Yamanaka et al. |

FOREIGN PATENT DOCUMENTS

| | | | |
|---|---|---|---|
| EP | 2202309 A1 | 6/2010 | |
| EP | 2419511 A1 | 2/2012 | |
| EP | 2734617 A1 | 5/2014 | |
| EP | 2888286 A1 | 7/2015 | |
| EP | 2917350 A1 | 9/2015 | |
| EP | 2734617 B1 | 4/2017 | |
| EP | 2419511 B1 | 1/2018 | |
| EP | 2888286 B1 | 2/2018 | |
| EP | 2917350 B1 | 4/2018 | |
| JP | 63044526 | 2/1988 | |
| WO | WO 97/35967 A2 | 10/1997 | |
| WO | WO 98/30683 A2 | 7/1998 | |
| WO | WO 99/05266 A2 | 2/1999 | |
| WO | WO 00/65137 A1 | 11/2000 | |
| WO | WO 01/00650 A1 | 1/2001 | |
| WO | WO 01/26454 A1 | 4/2001 | |
| WO | WO 2001/030978 A1 | 5/2001 | |
| WO | WO 01/46401 A1 | 6/2001 | |
| WO | WO 02097065 A2 * | 12/2002 | ........... C12N 5/0696 |
| WO | WO 03/018767 A2 | 3/2003 | |
| WO | WO 03/018780 A1 | 3/2003 | |
| WO | WO 03/046141 A2 | 6/2003 | |
| WO | WO 03/057836 A2 | 7/2003 | |
| WO | WO 03/100011 A2 | 12/2003 | |
| WO | WO 2005/049788 A2 | 6/2005 | |
| WO | WO 2006/052646 A1 | 11/2006 | |
| WO | WO 2007/019398 A1 | 2/2007 | |
| WO | WO 2007026255 A2 * | 3/2007 | ........... C12N 5/0696 |
| WO | WO 2007/047894 A2 | 4/2007 | |
| WO | WO 2008/103462 A2 | 8/2008 | |
| WO | WO 2009/133971 A1 | 11/2009 | |
| WO | WO 2009/157593 A1 | 12/2009 | |
| WO | WO 2010/050626 A1 | 5/2010 | |
| WO | WO 2010/137746 A1 | 12/2010 | |
| WO | WO 2011/016588 A1 | 2/2011 | |

OTHER PUBLICATIONS

Anokye-Danso et al., Cell Stem Cell, 8: 376-388, 2011.*
Alberio et al., Differential nuclear remodeling of mammalian somatic cells by Xenopus laevis oocyte and egg cytoplasm. Exp Cell Res. Jul. 1, 2005;307(1):131-41. Epub Apr. 7, 2005.
Ambrosi et al., Genome-wide reprogramming in hybrids of somatic cells and embryonic stem cells. Stem Cells. May 2007;25(5):1104-13. Epub Feb. 1, 2007.
Ambrosi et al., Reprogramming mediated by stem cell fusion. J Cell Mol Med. Apr.-Jun. 2005;9(2):320-30.
Bain et al., Embryonic stem cells express neuronal properties in vitro. Dev Biol. Apr. 1995;168(2):342-57.
Bodnar et al., Extension of life-span by introduction of telomerase into normal human cells. Science. Jan. 16, 1998;279(5349):349-52.
Brown et al., Alterations in chondrocyte cytoskeletal architecture during phenotypic modulation by retinoic acid and dihydrocytochalasin B-induced reexpression. J Cell Biol. Jan. 1988;106(1):171-9.
Byrne et al., Nuclei of adult mammalian somatic cells are directly reprogrammed to oct-4 stem cell gene expression by amphibian oocytes. Curr Biol. Jul. 15, 2003;13(14):1206-13.
Campbell, Nuclear equivalence, nuclear transfer, and the cell cycle. Cloning. 1999;1(1):3-15.
Chen et al., Embryonic stem cells generated by nuclear transfer of human somatic nuclei into rabbit oocytes. Cell Res. Aug. 2003;13(4):251-63.
Cohen et al., Induced differentiation in HT29, a human colon adenocarcinoma cell line. J Cell Sci. Aug. 1999;112 ( Pt 16):2657-66.
Collas et al., On the way to reprogramming cells to pluripotency using cell-free extracts. Reprod Biomed Online. Jun. 2006;12(6):762-70.
Collas, Cytoplasmic control of nuclear assembly. Reprod Fertil Dev. 1998;10(7-8):581-92.
Collas, Nuclear reprogramming in cell-free extracts. Philos Trans R Soc Lond B Biol Sci. Aug. 29, 2003;358(1436):1389-95.
Cowan et al,. Nuclear reprogramming of somatic cells after fusion with human embryonic stem cells. Science. Aug. 26, 2005;309(5739):1369-73.
Dimitrov et al., Remodeling somatic nuclei in Xenopus laevis egg extracts: molecular mechanisms for the selective release of histones H1 and H1(0) from chromatin and the acquisition of transcriptional competence. EMBO J. Nov. 1, 1996;15(21):5897-906.
Djuric et al., Epigenetics of induced pluripotency, the seven-headed dragon. Stem Cell Res Ther. Mar. 15, 2010;1(1):3. doi: 10.1186/scrt3.
Do et al., Nuclei of embryonic stem cells reprogram somatic cells. Stem Cells. 2004;22(6):941-9.
Dominko et al., Bovine oocyte cytoplasm supports development of embryos produced by nuclear transfer of somatic cell nuclei from various mammalian species. Biol Reprod. Jun. 1999;60(6):1496-502.
Fernandez-Valle et al., Actin plays a role in both changes in cell shape and gene-expression associated with Schwann cell myelination. J Neurosci. Jan. 1, 1997;17(1):241-50.
Ferreira et al., Calcineurin is associated with the cytoskeleton of cultured neurons and has a role in the acquisition of polarity. Mol Biol Cell. Dec. 1993;4(12):1225-38.
Fricker et al., Site-specific migration and neuronal differentiation of human neural progenitor cells after transplantation in the adult rat brain. J Neurosci. Jul. 15, 1999;19(14):5990-6005.
Gurdon et al., The future of cloning. Nature. Dec. 16, 1999;402(6763):743-6.
Hakelien et al., Novel approaches to transdifferentiation. Cloning Stem Cells. 2002;4(4):379-87.
Hamano et al., Functional studies on B cell hybridomas with B cell surface antigens. IV. Direct effects of cytochalasin B on differentiation. J Immunol. Jan. 1984;132(1):122-8.
Hammachi et al., Transcriptional activation by Oct4 is sufficient for the maintenance and induction of pluripotency. Cell Rep. Feb. 23, 2012;1(2):99-109. doi: 10.1016/j.celrep.2011.12.002. Epub Feb. 16, 2012.
Hansis et al., Nuclear reprogramming of human somatic cells by xenopus egg extract requires BRG1. Curr Biol. Aug. 24, 2004;14(16):1475-80.
Hayes et al., (The effects of cytochalasin B and colchicine on cell motility and ultrastructure in primary cultures of malignant gliomas. Acta Neuropathol. Oct. 13, 1978;44(1):21-30.
Hochedlinger et al., Ectopic expression of Oct-4 blocks progenitor-cell differentiation and causes dysplasia in epithelial tissues. Cell. May 6, 2005;121(3):465-77.
Holtzer et al., Effects of cytochaslasin B and colcemide on myogenic cultures. Proc Natl Acad Sci U S A. Feb. 1975;72(2):513-7.
Hornsby et al., Redifferentiation, cellular elongation and the cell surface during lens regeneration. J Embryol Exp Morphol. Jun. 1977;39:23-43.
Huangfu et al., Induction of pluripotent stem cells by defined factors is greatly improved by small-molecule compounds. Nat Biotechnol. Jul. 2008;26(7):795-7. doi: 10.1038/nbt1418. Epub Jun. 22, 2008.
Huangfu et al., Induction of pluripotent stem cells from primary human fibroblasts with only Oct4 and Sox2. Nat Biotechnol. Nov. 2008;26(11):1269-75. doi: 10.1038/nbt.1502. Epub Oct. 12, 2008.
Katagiri et al., Remodeling of sperm chromatin induced in egg extracts of amphibians. Int J Dev Biol. Jun. 1994;38(2):209-16.
Kikyo et al., Reprogramming nuclei: insights from cloning, nuclear transfer and heterokaryons. J Cell Sci. Jan. 2000;113 ( Pt 1):11-20.

(56) References Cited

OTHER PUBLICATIONS

Kim et al., Generation of human induced pluripotent stem cells by direct delivery of reprogramming proteins. Cell Stem Cell. Jun. 5, 2009;4(6):472-6. doi:10.1016/j.stem.2009.05.005. Epub May 28, 2009.
Kim et al., Oct4-induced pluripotency in adult neural stem cells. Cell. Feb. 6, 2009;136(3):411-9. doi: 10.1016/j.cell.2009.01.023.
Kishkina et al., [Differentiation of neuroblastoma cells caused by cytochalasin B]. Biull Eksp Biol Med. Jul. 1983;96(7):97-9.
Lanzendorf et al., Pregnancy following transfer of ooplasm from cryopreserved-thawed donor oocytes into recipient oocytes. Fertil Steril. Mar. 1999;71(3):575-7.
Lewitzky et al., Reprogramming somatic cells towards pluripotency by defined factors. Curr Opin Biotechnol. Oct. 2007;18(5):467-73.
Li et al., Nuclear transfer: progress and quandaries. Reprod Biol Endocrinol. Nov. 7, 2003;1:84.
Marshall et al., Nuclear envelope assembly after mitosis. Trends Cell Biol. Feb. 1997;7(2):69-74.
Matveeva et al., In vitro and in vivo study of pluripotency in intraspecific hybrid cells obtained by fusion of murine embryonic stem cells with splenocytes. Mol Reprod Dev. Jun. 1998;50(2):128-38.
Maxson et al., Differential stimulation of sea urchin early and late H2B histone gene expression by a gastrula nuclear extract after injection into Xenopus laevis oocytes. Mol Cell Biol. Mar. 1988;8(3):1236-46.
Meirelles et al., Complete replacement of the mitochondrial genotype in a Bos indicus calf reconstructed by nuclear transfer to a Bos taurus oocyte. Genetics. May 2001;158(1):351-6.
Mitalipov et al., Rhesus monkey embryos produced by nuclear transfer from embryonic blastomeres or somatic cells. Biol Reprod. May 2002;66(5):1367-73.
Monk et al., Human embryonic genes re-expressed in cancer cells. Oncogene. Dec. 6, 2001;20(56):8085-91.
Nakagawa et al., Generation of induced pluripotent stem cells without Myc from mouse and human fibroblasts. Nat Biotechnol. Jan. 2008;26(1):101-6. Epub Nov. 30, 2007.
Neri et al. Mouse fibroblasts are reprogrammed to Oct-4 and Rex-1 gene expression and alkaline phosphatase activity by embryonic stem cell extracts. Cloning Stem Cells. 2007 Fall;9(3):394-406.
NIH. Stem Cells: Scientific Progress and Future Research Directions, Department of Health and Human Services, Chapter 1, pp. 1-4, Jun. 2001.
Oliveri, Epigenetic dedifferentiation of somatic cells into pluripotency: cellular alchemy in the age of regenerative medicine? Regen Med. Sep. 2007;2(5):795-816.
Plath et al., Progress in understanding reprogramming to the induced pluripotent state. Nat Rev Genet. Apr. 2011;12(4):253-65. doi: 10.1038/nrg2955.
Prather et al., Nuclear transplantation in early pig embryos. Biol Reprod. Sep. 1989;41(3):414-8.
Sato et al., [Effects of A23187 and cytochalasin B on proliferation and differentiation of the cultured myoblasts]. Rinsho Shinkeigaku. Aug. 1991;31(8):809-14.
Sauman et al., Cytochalasin-D treatment triggers premature apoptosis of insect ovarian follicle and nurse cells. Int J Dev Biol. Sep. 1993;37(3):441-50.
Shea et al., Neuritogenesis in mouse NB2a/d1 neuroblastoma cells: triggering by calcium influx and involvement of actin and tubulin dynamics. Cell Biol Int Rep. Nov. 1990;14(11):967-79.
Simerly et al., Molecular correlates of primate nuclear transfer failures. Science. Apr. 11, 2003;300(5617):297.
Smith et al., Cytoplasmic transfer of the mitogenic response to platelet-derived growth factor. Proc Natl Acad Sci U S A. Jul. 1981;78(7):4363-7.
Sullivan et al., Elucidating nuclear reprogramming mechanisms: taking a synergistic approach. Reprod Biomed Online. Jan. 2008;16(1):41-50.
Tada et al., Embryonic germ cells induce epigenetic reprogramming of somatic nucleus in hybrid cells. EMBO J. Nov. 3, 1997;16(21):6510-20.
Tada et al., Pluripotency of reprogrammed somatic genomes in embryonic stem hybrid cells. Dev Dyn. Aug. 2003;227(4):504-10.
Takahashi et al., Induction of pluripotent stem cells from adult human fibroblasts by defined factors. Cell. Nov. 30, 2007;131(5):861-72.
Takahashi et al., Induction of pluripotent stem cells from mouse embryonic and adult fibroblast cultures by defined factors. Cell. Aug. 25, 2006;126(4):663-76. Epub Aug. 10, 2006.
Takigawa et al., Cytoskeleton and differentiation: effects of cytochalasin B and colchicine on expression of the differentiated phenotype of rabbit costal chondrocytes in culture. Cell Differ. Aug. 1984;14(3):197-204.
Tamai et al., Cytochalasin B inhibits morphogenetic movement and muscle differentiation of activin-treated ectoderm in Xenopus. Dev Growth Differ. Feb. 1999;41(1):41-9.
Thesignh et al., Transdifferentiation of hypertrophic chondrocytes into osteoblasts in murine fetal metatarsal bones, induced by co-cultured cerebrum. Bone Miner. Jan. 1991;12(1):25-40.
Thiebot et al., Drug-induced alterations in rat peritubular cell cytoskeleton result in proteoglycan synthesis modifications. Comparison with some intracellular signaling pathways. Biol Cell. Mar. 1999;91(2):117-29.
Thomson et al., Embryonic stem cell lines derived from human blastocysts. Science. Nov. 6, 1998;282(5391):1145-7.
Thomson et al., Isolation of a primate embryonic stem cell line. Proc Natl Acad Sci U S A. Aug. 15, 1995;92(17):7844-8.
Tung et al., Characterization of rat testicular peritubular myoid cells in culture: alpha-smooth muscle isoactin is a specific differentiation marker. Biol Reprod. Feb. 1990;42(2):351-65.
Ulloa et al., Involvement of gamma and beta actin isoforms in mouse neuroblastoma differentiation. Eur J Neurosci. Jul. 1996;8(7):1441-51.
Unemori et al., Reorganization of polymerized actin: a possible trigger for induction of procollagenase in fibroblasts cultured in and on collagen gels. J Cell Biol. Sep. 1986;103(3):1021-31.
Wade et al., Chromatin remodeling in nuclear cloning. Eur J Biochem. May 2002;269(9):2284-7.
Wangh et al., Efficient reactivation of Xenopus erythrocyte nuclei in Xenopus egg extracts. J Cell Sci. Jun. 1995;108 ( Pt 6):2187-96.
Wernig et al., In vitro reprogramming of fibroblasts into a pluripotent ES-cell-like state. Nature. Jul. 19, 2007;448(7151):318-24. Epub Jun. 6, 2007.
Willadsen, Nuclear transplantation in sheep embryos. Nature. Mar. 6-12, 1986;320(6057):63-5.
Wilmut et al., Viable offspring derived from fetal and adult mammalian cells. Nature. Feb. 27, 1997;385(6619):810-3.
Yu et al., Induced pluripotent stem cell lines derived from human somatic cells. Science. Dec. 21, 2007;318(5858):1917-20. Epub Nov. 20, 2007.
Yujiri et al., MEK kinase 1 (MEKK1) transduces c-Jun NH2-terminal kinase activation in response to changes in the microtubule cytoskeleton. J Biol Chem. Apr. 30, 1999;274(18):12605-10.
Zanetti et al., Induction of chondrogenesis in limb mesenchymal cultures by disruption of the actin cytoskeleton. J Cell Biol. Jul. 1984;99(1 Pt 1):115-23.
Zhu et al., Reprogramming of human primary somatic cells by OCT4 and chemical compounds. Cell Stem Cell. Dec. 3, 2010;7(6):651-5. doi: 10.1016/j.stem.2010.11.015.
Ziegler et al., Phenotypic expression of malignancy in hybrid and cybrid mouse cells. Somatic Cell Genet. Jul. 1978;4(4):477-89.
Zinzar et al., Azacytidine plus verapamil induces the differentiation of a newly characterized biphenotypic human myeloid-B lymphoid leukemic cell line BW-90. Leuk Res. Aug. 1998;22(8):677-85.
[No Author Listed] New human embryonic stem cell line now available from ATCC's stem cell center. ATCC: The Essentials of Life Science Research Press Release. Manassas, VA. Dec. 8, 2004. Accessed online www.atcc.org/NewHumanEmbryonicStemCellLine/tabid/757/Default.aspx. 2 pages.

(56) References Cited

OTHER PUBLICATIONS

Frost et al., The importance of imprinting in the human placenta. PloS Genet. Jul. 1, 2010;6(7):e1001015. doi: 10.1371/journal.pgen.1001015. Review.

Gibbs et al., Evolutionary and biomedical insights from the rhesus macaque genome. Science. Apr. 13, 2007;316(5822):222-34.

Krivokharchenko et al., Development of parthenogenetic rat embryos. Biol Reprod. Mar. 2003;68(3):829-36.

Kure-Bayashi et al., Successful implantation of in vitro-matured, electro-activated oocytes in the pig. Theriogenology. Mar. 15, 2000;53(5):1105-19.

Loi et al., Development of parthenogenetic and cloned ovine embryos: effect of activation protocols. Biol Reprod. May 1998;58(5):1177-87.

Marshall et al., Parthenogenetic activation of marmoset (*Callithrix jacchus*) oocytes and the development of marmoset parthenogenones in vitro and in vivo. Biol Reprod. Dec. 1998;59(6):1491-7.

Ozil et al., Activation of rabbit oocytes: the impact of the Ca2+ signal regime on development. Development. Mar. 2001;128(6):917-28.

Reik et al., Genomic imprinting: parental influence on the genome. Nat Rev Genet. Jan. 2001;2(1):21-32. Review.

Solter, Differential imprinting and expression of maternal and paternal genomes. Annu Rev Genet. 1988;22:127-46. Review.

Sturm et al., Abnormal development of embryonic and extraembryonic cell lineages in parthenogenetic mouse embryos. Dev Dyn. Sep. 1994;201(1):11-28.

Surani et al., Development of gynogenetic eggs in the mouse: implications for parthenogenetic embryos. Science. Dec. 2, 1983;222(4627):1034-6.

Kato et al., Developmental potential of mouse follicular epithelial cells and cumulus cells after nuclear transfer. Biol Reprod. Oct. 1999;61(4):1110-4.

Kwon et al., Production of Live Young by Serial Nuclear Tranfer with Mitotic Stages of Donor Nuclei in Mic. J Reproduct Dev. 1997;43(1):25-31.

Lanza et al., Extension of cell life-span and telomere length in animals cloned from senescent somatic cells. Science. Apr. 28, 2000;288(5466):665-9.

Polejaeva et al., Cloned pigs produced by nuclear transfer from adult somatic cells. Nature. Sep. 7, 2000;407(6800):86-90.

Stojkovic et al., Derivation of a human blastocyst after heterologous nuclear transfer to donated oocytes. Reprod Biomed Online. Aug. 2005;11(2):226-31.

Taranger et al., Induction of dedifferentiation, genomewide transcriptional programming, and epigenetic reprogramming by extracts of carcinoma and embryonic stem cells. Mol Biol Cell. Dec. 2005;16(12):5719-35. Epub Sep. 29, 2005.

Tsunoda et al, Full-term development after transfer of nuclei from 4-cell and compacted morula stage embryos to enucleated oocytes in the mouse. J Exp Zool. Jul. 1, 1997;278(4):250-4.

Wakayama et al., Full-Term Development of Mice from Enucleated Oocytes Injected with Cumulus Cell Nuclei. Nature. Jul. 23, 1998;394:369-74.

\* cited by examiner

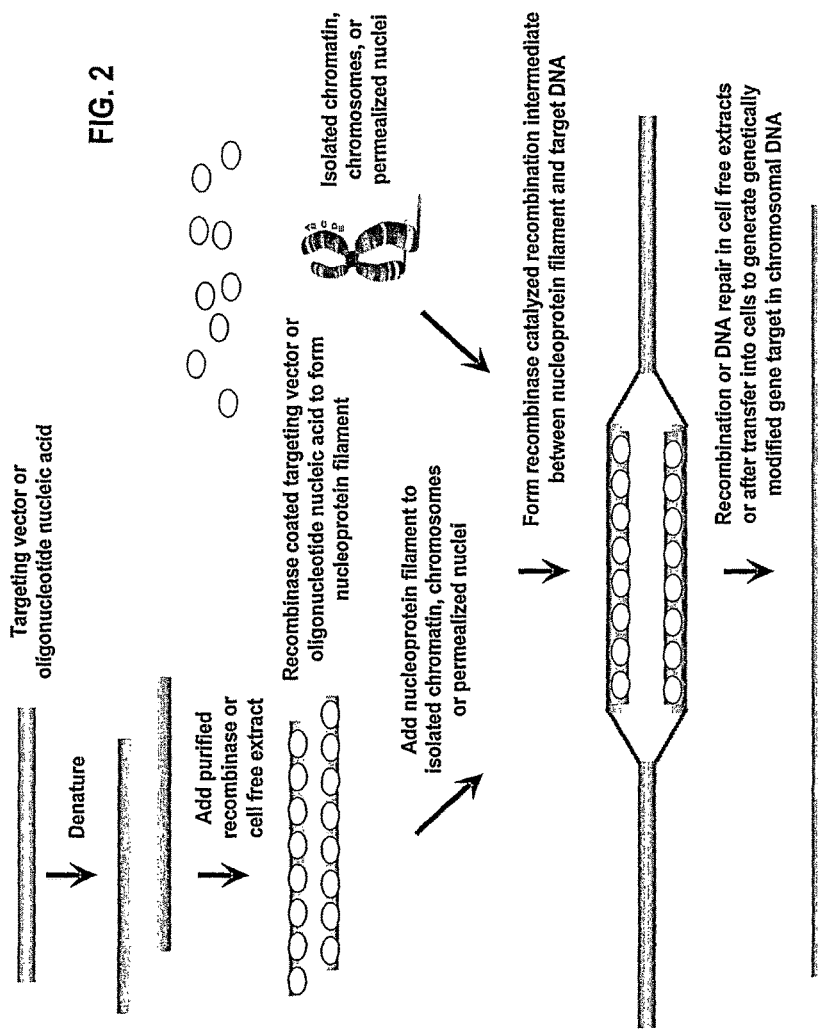

METHODS OF REPROGRAMMING ANIMAL SOMATIC CELLS

RELATED APPLICATIONS

This application is a continuation of U.S. patent application Ser. No. 11/989,988 filed on Mar. 8, 2010, which is a national stage filing under 35 U.S.C. § 371 of International Application No. PCT/US2006/030632 filed on Aug. 3, 2006, which was published under PCT Article 21(2) in English, and which claims the benefit under 35 U.S.C. § 119(e) to U.S. provisional application No. 60/705,625 filed Aug. 3, 2005, U.S. provisional application No. 60/729,173 filed Oct. 20, 2005, and U.S. provisional application No. 60/818,813 filed Jul. 5, 2006, the disclosures of which are all incorporated in their entirety by reference.

FIELD OF THE INVENTION

This invention generally relates to methods of reprogramming an animal somatic cell from a particular differentiated state to another state, and the use of such cells and tissues in the treatment of human diseases and age-related conditions. More particularly, the invention relates to an improved method utilizing a three-step process whereby the nuclear envelope of the somatic cell nucleus is first remodeled to that of an undifferentiated cell or a germ-line cell prior to the second step of transferring the remodeled nucleus into the cytoplasm of an oocyte or an undifferentiated cell. This nuclear remodeling step markedly enhances the efficiency of cellular reconstitution when the remodeled nucleus is transferred into embryonic or germ-line cytoplasm for the purpose of stem cell derivation. In addition, the removal of components of the nuclear envelope specific for differentiated cells, such as lamin A, and the reprogramming of chromatin results in a reactivation of telomerase activity, a lengthening of telomere length, and mechanisms of homologous recombination that repair tandemly-repeated DNA sequences. When pluripotent stem cells are derived by the present invention, they may be utilized in novel therapeutic strategies in the treatment of cardiac, neurological, endocrinological, vascular, retinal, dermatological, muscular-skeletal disorders, and other diseases.

BACKGROUND OF THE INVENTION

Advances in stem cell technology, such as the isolation and use of human embryonic stem (hES) cells, have become an important new subject of medical research. hES cells have a demonstrated potential to differentiate into any and all of the cell types in the human body, including complex tissues. This ability of hES cells has led to the suggestion that many diseases resulting from the dysfunction of cells may be amenable to treatment by the administration of hES-derived cells of various differentiated types (Thomson et al., Science 282:1145-7, (1998)). Nuclear transfer studies have demonstrated that it is possible to transform a somatic differentiated cell back to a totipotent state such as that of ES or ED cells (Cibelli et al., Nature Biotech 16:642-646, (1998)). The development of technologies to reprogram somatic cells back to a totipotent ES cell state such as by nuclear transfer offers a means to deliver ES-derived somatic cells with a nuclear genotype of the patient (Lanza et al., Nature Medicine 5:975-977, (1999)). It is expected that such cells and tissues would not be rejected, despite the presence of allogeneic mitochondria (Lanza et al., Nature Biotech 20:689-696, (2002)). Nuclear transfer also allows the rebuilding of telomere repeat length in cells through the reactivation of the telomerase catalytic component in the early embryo (Lanza et al., Science 288:665-669, (2000)). Nevertheless, there remains a need for improvements in methods to reprogram animal cells that increase the frequency of successful and complete reprogramming and reduce the dependence on the availability of human oocytes.

Because of the relative difficulty of obtaining large numbers of human oocytes, there has been considerable interest in determining whether other germ-line cells, such as cultured ES cells, or cytoplasm from said cells, could be used to reprogram somatic cells. Such cells would have an important advantage over oocytes as a means of inducing reprogramming in that they can be easily expanded in number in vitro. The restoration of expression of at least some measured embryonic-specific genes has been observed in somatic cells following fusion with ES cells (Do and Scholer, Stem Cells 22:941-949, (2004); Do and Scholer, Reprod. Fertil. Dev. 17:143-149, (2005)). However, the resulting cells are hybrids, often with a tetraploid genotype, and therefore not suited as normal or histocompatible cells for transplant purposes. Indeed, one of the proposed purposes of generating autologous totipotent cells is to prevent the rejection of ES-derived cells. Using the techniques described in these published studies, the ES cells used to reprogram a patient's cell would therefore likely add alleles that could generate an immune response leading to rejection. Nevertheless, the evidence that ES cells can reprogram somatic cell chromosomes has excited researchers and generated a new field of research called "fusion biology" (Dennis, Nature 426:490-491, (2003)).

Another potential source of cells capable of reprogramming human somatic cells with a greater ease of availability than human oocytes are oocytes of animal species. The demonstration of the restoration of totipotency in somatic cells by nuclear transfer across species (Lanza et al., Cloning 2:79-90, (2000)) opens the possibility of identifying animal oocytes that can be easily obtained for use in reprogramming human cells (Byrne et al., Curr Biol 13:1206-1213, (2003)). However, likely because of molecular differences between the species, cross species nuclear transfer, although possible, is often even more inefficient than same-species nuclear transfer.

Among the many molecular alterations that occur following somatic cell nuclear transfer, some of the more critical alterations are the reprogramming of the chromatin through poorly-understood mechanisms in the recipient oocyte and remodeling of the proteins of the nuclear envelope. The nuclear envelope includes the inner nuclear membrane (INM) and outer nuclear membrane (ONM), nuclear pore complexes (NPCs), and nuclear lamina. The proteins of the nuclear envelope, in particular those proteins of the lamina, differ between somatic and germ-line cells and play an important role in regulating the cell cycle, monitoring DNA damage checkpoint pathways, and regulating cell differentiation. In particular, the protein subunits of the lamina include the type V intermediate filament proteins, lamin A/C and B, which form a meshwork internal to the INM (Foisner, J. Cell Sci. 114:3791-3792, (2001)). Some of these proteins, such as lamin A/C, play an important role in regulating chromosomal integrity, DNA damage checkpoints, and telomere status signaling through their interactions with the WRN helicase, POT1, Tel1, and Tel2. In germ-line cells that are telomerase positive, or where telomerase is utilized, the nuclear matrix lacks lamin A/C or otherwise allows tandemly-repeated sequences of DNA to be repaired and, in the case of the telomere, to be lengthened by telomerase. Other proteins associated with the INM include the family of lamina associated polypeptides (LAPs) including lamina-associated protein 1 (LAP1, of which there are at least three isoforms ($\alpha$, $\beta$, and $\gamma$)), LAP2 (with at least six isoforms) and emerin (which when mutated leads to abnormal muscle differentiation and Emery-Dreifuss muscular dystrophy). Other proteins associated with the INM include the ring finger binding protein (RFBP), otefin, germ cell-less (GCL) and nurim. The lamins are known to play an important role in regulating the function of transcriptional regulators such as the retinoblastoma protein (pRB) and LBR which in turn can bond heterochromatin protein 1 (HP1). By way of example of the need to remodel the nuclear envelope in order to reprogram a differentiated somatic cell to an undifferentiated state, undifferentiated germ-line cells generally lack the presence of lamin A, while germ-line cells contain proteins such as germ cell-less (GCL) and lamin C2, which are often not expressed in differentiated somatic cells (Furukawa et al., Exp. Cell Res. 212:426-430, 1994). Incomplete remodeling of the nuclear envelope would contribute to the inefficiency or incomplete reprogramming of cells using existing technologies.

Therefore, each of the technologies to reprogram human somatic cells known in the art have their own unique difficulties. SCNT provides a satisfactory level of reprogramming but is limited by the number of human oocytes available to researchers. Cross-species nuclear transfer and cell fusion technologies are not generally limited in the cells used in reprogramming but are limited by the degree of successful reprogramming or the robustness of the growth of the resulting reprogrammed cells. Therefore, there remains a need for improved technologies to both increase the frequency and quality of reprogramming of differentiated somatic cells and of producing reprogrammed cells that are capable of expansion in vitro in order to obtain a useful number of cells for research, testing for quality control, and for use in cell therapy. The present invention combines aspects of several existing technologies already known in the art in a novel and non-obvious manner to provide a means of reprogramming differentiated cells as effectively or more effectively than SCNT and to provide a more acceptable and cost-effective substitute for oocytes as the vehicle for reprogramming. The present invention achieves these goals in part by using cells that are easily and inexpensively obtained in unlimited quantities and a technology that can be scaled such that thousands or millions of fusions can be performed simultaneously, thereby increasingly the probability of a successful final outcome. Additionally, the present invention provides a technique that facilitates the reactivation of telomerase and an extension of telomere length, thereby restoring cell replicative lifespan. The present invention further provides an assay that allows for the analysis of what components in undifferentiated and germ-line cells are critical for nuclear reprogramming. The invention also provides a procedure that can be automated through robotics to reduce cost and improve quality control.

SUMMARY OF THE INVENTION

The present invention provides methods for the reprogramming of animal somatic cells and methods for the derivation, formulation, and use of the resulting reprogrammed cells and engineered tissues in modalities of therapy for the prevention and treatment of disease. More specifically, the invention provides an improved means of reprogramming differentiated cells to an undifferentiated state, extending telomere length and therefore replicative lifespan, and accordingly producing stem cells and resulting differentiated cells of many kinds with a nuclear genotype identical to the genotype of the original differentiated cell. The present invention may be used to analyze the mechanisms of nuclear reprogramming and or the production of differentiated cells for use in research and therapy.

The methods of this invention represent an improvement over existing techniques, such as human somatic cell nuclear transfer (SCNT), used to de-differentiate animal somatic cells into an embryonic state, thereby producing hES cells. The present invention provides methods to improve such existing techniques by separating cellular reprogramming into at least two, or preferably three, separate steps, utilizing in some of those steps cytoplasmic components from a donor cell source, wherein the donor source is a differentiated cell from a species different from the species of the oocyte. Using a donor cell source from a different species than the species of the oocyte eases access to reprogramming materials, the degree of successful reprogramming, and the scale-up of the process of reprogramming differentiated cells.

In one embodiment of the invention, somatic differentiated cells are reprogrammed to an undifferentiated state through a novel reprogramming technique comprised of the following three steps:

In the first step, designated the nuclear remodeling step, the degree of reprogramming of the somatic cell genome is increased and the problem of access to oocytes of the same species as the somatic cell is alleviated by the use of any or a combination of several novel reprogramming procedures. In all of these novel procedures, the somatic cell nucleus is remodeled to replace the components of the nuclear envelope with the components of an undifferentiated cell. Simultaneously, or at a point in time early enough to prevent the incorporation of somatic cell differentiated components into the nuclear envelope, the chromatin of said cell is reprogrammed to express genes of an undifferentiated cell. The first step is advantageous over current SCNT technology in that oocytes of the same species as the somatic cell are not required; further, an improved quality of reprogramming can be achieved.

In the second step, designated herein as the cellular reconstitution step, the nucleus, containing the remodeled nuclear envelope of step one, is either transferred to an enucleated cytoplasm of an undifferentiated embryonic cell, or is fused with a cytoplasmic bleb containing a requisite mitotic apparatus which is capable, together with the transferred nucleus, of producing a population of undifferentiated stem cells such as ES or ED-like cells capable of proliferation. The second step has the advantage over SCNT in that a large number of nuclei or chromosome clumps remodeled in step one may be simultaneously fused with cytoplasmic blebs in step two to increase the probability of obtaining reprogrammed cells capable of successfully proliferating in vitro, resulting in a large number of cultured reprogrammed cells.

In the third step, colonies of cells arising from one or a number of cells resulting from step two are characterized for the extent of reprogramming and for the normality of the karyotype and colonies of a high quality are selected. While this third step is not required to successfully reprogram cells and is not necessary in some applications of the present invention, such as in analyzing the molecular mechanisms of reprogramming, for many uses, such as when reprogramming cells for use in human transplantation, the inclusion of the third quality control step is preferred. Colonies of reprogrammed cells that have a normal karyotype but not a sufficient degree of reprogramming may be recycled by repeating steps 1-2 or 1-3.

In another embodiment of the invention, the nucleus is remodeled in step one by the transfer of one or numerous permeabilized or nonpermeabilized somatic cells into an oocyte of another species. The resulting remodeled nucleus or nuclei are then removed and further processed in steps two and three.

In another embodiment of the invention, the genome of a somatic cell is remodeled in step one by condensation to a chromosome clump through the exposure of isolated somatic cell nuclei to an extract from mitotic cells, such as metaphase II oocytes, metaphase germ-line cells such as the EC cell line NTera-2, or of mitotic somatic cells of the same or different species. Said chromosome clumps are then further processed in steps two and three and the previous steps repeated if the cells do not show an acceptable degree of reprogramming.

In another embodiment of the invention, the genome of a somatic cell is remodeled in step one by condensation to a chromosome clump through the exposure of isolated somatic cell nuclei to an extract from mitotic cells, such as metaphase II oocytes, metaphase germ-line cells such as the EC cell line NTera-2, or of mitotic somatic cells of the same or different species. Said chromosome clumps are then subsequently encapsulated in a new nuclear envelope in vitro using extracts from undifferentiated cells. The resulting remodeled nuclei are then further processed in steps two and three and the previous steps repeated if the cells do not show an acceptable degree of reprogramming. Additionally, the remodeled nuclei and cells may be used in assays to analyze the mechanisms of reprogramming.

In another embodiment of the invention, one or more factors expressed in undifferentiated cells (e.g., EC cells, ES cells, etc.) are transiently expressed or overexpressed in the undifferentiated cell extracts or cells of step 1 and/or step 2 or are added as proteins to said cell extracts. Expression of these factors may confer characteristics of an undifferentiated cell to the somatic cell and facilitate reprogramming of the somatic cell. Such factors include, for example, NANOG, SOX2, DNMT3B, CROC4, H2AFX, HIST1H2AB, HIST1H4J, HMGB2, LEFTB, MYBL2, MYC, MYCN, NANOG, OCT3/4 (POU5F1), OTX2, SALL4, TERF1, TERT, ZNF206, or any other factors (such as transcriptional regulators) that confer characteristics of an undifferentiated cell state. Further, any number or combinations of the above-mentioned factors may be used.

In another embodiment of the invention, the various kinds of in vitro reprogramming of step one of the present invention are utilized as an in vitro model of nuclear reprogramming useful in analyzing the molecular mechanisms of reprogramming. For example, particular molecular components may be added or deleted from the extract to determine the role of certain components in reprogramming.

In another embodiment of the invention, the various components determined to play an important role in reprogramming identified in the above assay or by other means are then correspondingly incorporated or deleted from the reprogramming extract to increase the efficiency of reprogramming in the same or cross species reprogramming protocol. Such molecules include but are not limited to human protein components, purified RNA, including miRNA from oocytes, blastomeres, morulae, ICMs, embryonic disc, ES cells, EG cells, EC cells, or other germ-line cells. The components may be added or deleted during any of steps 1-3. Particular components may be deleted by methods such as, for example, immunoprecipitation.

In another embodiment of the invention, steps 1-2 are repeated as step one followed by step two, followed by step one, followed by step two, until characterization in step three demonstrates successful reprogramming of the somatic cells.

In another aspect of the invention, cytoplasts from undifferentiated or germ-line cells are depleted of mitochondria to make cell lines into which donor cell mitochondria may be added before, during, or after step two to result in reprogrammed cells wherein the mitochondrial genotype as well as the nuclear genotype is identical to the donor differentiated cell.

In another embodiment of the invention, undifferentiated cell factors such as, for example, SOX2, NANOG, DNMT3B, CROC4, H2AFX, HIST1H2AB, HIST1H4J, HMGB2, LEFTB, MYBL2, MYC, MYCN, NANOG, OCT3/4 (POU5F1), OTX2, SALL4, TERF1, TERT, ZNF206, are added to the cytoplasts or cytoplasmic blebs from undifferentiated or germ-line cells of step 2. In particular embodiments, two, three, four, or five of the factors are added to the cytoplasts. In other embodiments, six or more of the factors are added to the cytoplasts.

In another aspect of the invention, reprogrammed cells resulting from the use of steps 1-2 or 1-3 are differentiated in a variety of in vitro, in vivo, or in ovo differentiation conditions to yield cells of any or a combination of the three primary germ layers endoderm, mesoderm, or ectoderm, including complex tissues such as tissues formed in teratomas. In certain embodiments, differentiated cell types are derived from the reprogrammed cells of the present invention without the generation of an ES cell line. For example, differentiated cells may be obtained by culturing undifferentiated reprogrammed cells in the presence of at least one differentiation factor and selecting differentiated cells from the culture. Selection of differentiated cells may be based on phenotype, such as the expression of certain cell markers present on differentiated cells, or by functional assays (e.g., the ability to perform one or more functions of a particular differentiated cell type). Differentiated cells derived by the methods of the present invention include, but are not limited to, pancreatic beta cells and pancreatic precursor cells.

In another embodiment, the cells reprogrammed according to the present invention are genetically modified through the addition, deletion, or modification of their DNA sequence(s). Such modifications can be made by the random incorporation of an exogenous vector, by gene targeting, or through the use of artificial chromosomes.

In another embodiment of the present invention, the nucleus being remodeled in step one is modified by the addition of extracts from cells such as, for example, DT40, known to have a high level of homologous recombination. The addition of DNA targeting constructs and the extracts from cells permissive for a high level of homologous recombination will then yield cells after reconstitution in step 2 and screening in step 3 that have a desired genetic modification.

Another embodiment of the invention is a business model for commercializing cells produced from the use of said invention. The business model includes the transfer of human somatic differentiated cells to regional centers where the reprogramming steps 1, 2, 1-2 or 1-3 are performed.

In another embodiment of the invention, the differentiated somatic cells or the reprogrammed cells resulting from the application of steps 1, 2, 1-2 or 1-3 are cryopreserved and banked for future use.

In another embodiment of the present invention, the reprogrammed cells resulting from the application of steps 1, 2, 1-2, or 1-3 are shipped to health care facilities where they are differentiated into medically useful cell types for use in research and transplantation.

In another embodiment of the present invention, kits containing ingredients useful in performing the activities of steps 1, 2, or 3 are shipped to research, biomedical, or health care facilities where they are used to reprogram differentiated cells into cell types for use in research and transplantation.

In another embodiment of the present invention, the reprogrammed cells resulting from the application of steps 1, 2, 1-2, or 1-3 are shipped to health care facilities after having been differentiated into a useful composition of cell types.

Other features and advantages of the invention will be apparent from the following description and from the claims.

DESCRIPTION OF THE DRAWINGS

FIG. 2 shows a diagram displaying the modification of isolated chromosomes, chromatin, or nuclei in vitro. Purified recombinase or cell free extract is shown as spheres.

DESCRIPTION OF THE INVENTION

Figure 1:
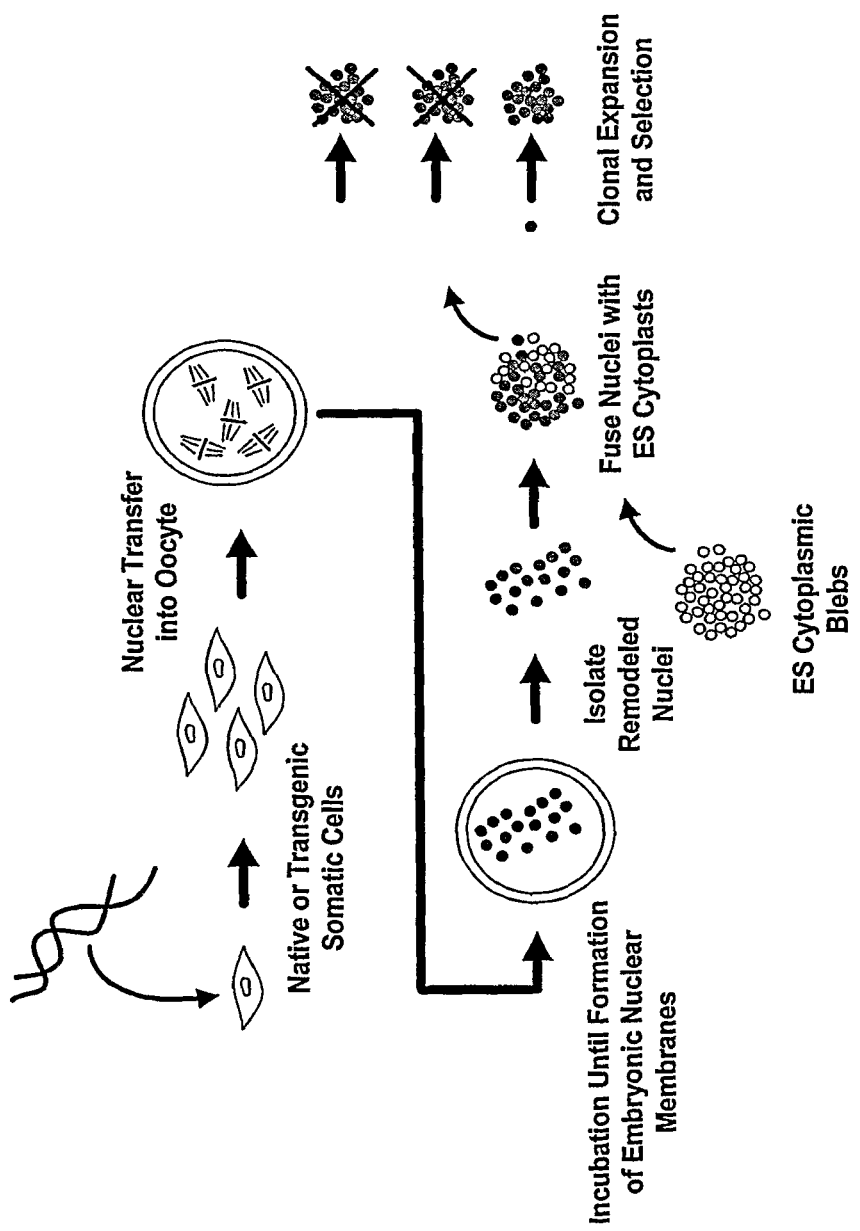
FIG. 1 shows the remodeling of multiple somatic cell nuclei within one oocyte, the subsequent lysing of the oocyte to retrieve remodeled nuclei, and their fusion with ES cell cytoplasmic blebs to yield ES cell lines.

Table of Abbreviations
  CT—Chromatin Transfer
  CyT—Cytoplasmic Transfer
  DMAP—Dimethylaminopurine
  EC Cells—Embryonal Carcinoma Cells
  ED Cells—Embryo-derived cells are cells derived from a zygote, blastomeres, morula or blastocyst-staged mammalian embryo produced by the fusion of a sperm and egg cell, nuclear transfer, parthenogenesis, or the reprogramming of chromatin and subsequent incorporation of the reprogrammed chromatin into a plasma membrane of an oocyte or blastomere to produce a cell line. The resulting cell line may be either a differentiated cell line or the cells may be maintained as undifferentiated ES cells. Therefore ED cells are inclusive of ES cells and cells derived by directly differentiating cells from a mammalian preimplantation embryo. hED Cells are human embryo-derived cells derived from, for example, human preimplantation embryos. Human embryo-derived cells may refer to morula-derived cells, blastocyst-derived cells including those of the inner cell mass, embryonic shield, or epiblast, or other totipotent or pluripotent stem cells of the early embryo, including primitive endoderm, ectoderm, and mesoderm and their derivatives, but excluding hES cells that have been passaged as cell lines. The hED cells may be derived from fertilization of an egg cell with sperm or DNA, nuclear transfer, parthenogenesis, or by means to generate hES cells with homozygosity in the HLA region.
  ES Cell—Embryonic stem cells derived from a zygote, blastomeres, morula or blastocyst-staged mammalian embryo produced by the fusion of a sperm and egg cell, nuclear transfer, parthenogenesis, or the reprogramming of chromatin and subsequent incorporation of the reprogrammed chromatin into a plasma membrane to produce a cell. hES Cells are human embryonic stem cells, derived from, for example, human preimplantation embryos. hES Cells may be derived from the inner cell mass of human blastocysts or morulae that have been serially passaged as cell lines. The hES cells may be derived from fertilization of an egg cell with sperm or DNA, nuclear transfer, parthenogenesis, or by means to generate hES cells with homozygosity in the HLA region.
  GCL—Germ cell-less
  HSE—Human skin equivalents are mixtures of cells and biological or synthetic matrices manufactured for testing purposes or for therapeutic application in promoting wound repair.
  ICM—Inner cell mass of the mammalian blastocyst-stage embryo.
  INM—Inner nuclear membrane
  MBS—Magnesium buffered saline
  MiRNA—Micro RNA
  NPC—Nuclear Pore Complex
  NT—Nuclear Transfer
  ONM—Outer nuclear membrane
  PEG—Polyethylene glycol
  PS fibroblasts—Pre-scarring fibroblasts are fibroblasts derived from the skin of early gestational skin or derived from ED cells that display a prenatal pattern of gene expression with that they promote the rapid healing of dermal wounds without scar formation.
  SCNT—Somatic Cell Nuclear Transfer
  SLO—Streptolysin O
  SPF—Specific Pathogen-Free The present invention provides improved methods for the reprogramming of differentiated cells to a more pluripotent state by utilizing a multiple-step procedure that includes a distinct nuclear remodeling step and a cellular reconstitution step.

The term "cellular reconstitution" refers to the transfer of a nucleus or chromatin to cellular cytoplasm so as to obtain a functional cell.

The term "chromatin transfer" (CT) refers to the cellular reconstitution of condensed chromatin.

The term "condensed chromatin" refers to DNA not enclosed by a nuclear envelope. Condensed chromatin my result, for example, by exposing a nucleus to a mitotic extract such as from an M1 or an MII oocyte or other mitotic cell extract, by transferring a nucleus into an M1 or an MII oocyte or other mitotic cell and retrieving the resulting condensed chromatin following the breakdown of the nuclear envelope. Condensed chromatin refers to chromosomes that are in a greater degree of compaction than the degree of compaction that occurs in any phase of the cell cycle other than metaphase.

The term "cytoplasmic bleb" refers to the cytoplasm of a cell bound by an intact, or permeabilized, but otherwise intact plasma membrane but lacking a nucleus. It is used interchangeably and synonymously with the term "enucleate cytoplast" and "enucleate(d) cytoplasm", unless the term "enucleate cytoplasm" is explicitly used in the context of an extract in which the plasma membrane has been removed.

The term "cytoplasmic transfer" (CyT) refers to any number of techniques known in the art for juxtaposing the nucleus of a somatic cell with the cytoplasm of an undifferentiated cell. Such techniques include, but are not limited to, the direct transfer of said undifferentiated cytoplasm into the cytoplasm of a differentiated cell, the permeabilization of a somatic cell to allow the diffusion of undifferentiated cell cytoplasm into the somatic cell, or the transfer of the somatic cell nucleus into a cytoplasmic bleb of an undifferentiated cell.

The term "cytoplasmic transfer" refers to the juxtaposition of the genome of a differentiated cell with the cytoplasm of an undifferentiated cell. This can be accomplished in a number of ways including the permeabilization of a somatic cell and exposure of the permeabilized cell(s) to extracts of undifferentiated cells, the microinjection of the cytoplasm of undifferentiated cells into the cytoplasm of The term "differentiated cell" refers to any cell from any vertebrate species in the process of differentiating into a somatic cell lineage or having terminally differentiated into the type of cell it will be in the adult organism.

The term "pluripotent stem cells" refers to animal cells capable of differentiating into more than one differentiated cell type. Such cells include ES cells, EG cells, EDCs, ED-like cells, and adult-derived cells including mesenchymal stem cells, neuronal stem cells, and bone marrow-derived stem cells. Pluripotent stem cells may be genetically modified or not genetically modified. Genetically modified cells may include markers such as fluorescent proteins to facilitate their identification within the egg.

The term "embryonic stem cells" (ES cells) refers to, for example, cells derived from the inner cell mass of blastocysts or morulae that have been serially passaged as cell lines. The ES cells may be derived from fertilization of an egg cell with sperm or DNA, nuclear transfer, parthenogenesis or by means to generate ES cells with homozygosity in the MHC region. hES cells are human ES Cells.

The term "fusigenic compound" refers to a compound that increases the likelihood that a condensed chromatin or nucleus is fused with and incorporated into a recipient cytoplasmic bleb resulting in a viable cell capable of subsequent cell division. Such fusigenic compounds may, by way of nonlimiting example, increase the affinity of a condensed chromatin or a nucleus with the plasma membrane. Alternatively, the fusigenic compound may increase the likelihood of the joining of the lipid bilayer of the target cytoplasmic bleb with the condensed chromatin, nuclear envelope of an isolated nucleus, or the plasma membrane of a donor cell.

The term "heteroplasmon" refers to a cell resulting from the fusion of a cell containing a nucleus and cytoplasm with the cytoplast of another cell.

The term "human embryo-derived cells" (hEDC) refer to blastomeres, morula-derived cells, blastocyst-derived cells including those of the inner cell mass, embryonic shield, or epiblast, or other totipotent or pluripotent stem cells of the early embryo, including primitive endoderm, ectoderm, and mesoderm and their derivatives, but excluding hES cells that have been passaged as cell lines. The hEDC cells may be derived from fertilization of an egg cell with sperm or DNA, nuclear transfer, parthenogenesis, or by means to generate hES cells with homozygosity in the HLA region.

The term "human embryo-derived-like cells" (hED-like) refer to pluripotent stem cells produced by the present invention that are not cultured so as to retain the characteristics of ES cells, but like morula-derived cells, blastocyst-derived cells including those of the inner cell mass, embryonic shield, or epiblast, or other totipotent or pluripotent stem cells of the early embryo, including primitive endoderm, ectoderm, and mesoderm and their derivatives that have not been cultured so as to maintain stable hES lines, are capable of differentiating into any of the somatic cell differentiated types. The hED-like cells may be derived with genetic modifications, including modified so as to lack genes of the MHC region, to be hemizygous or homozygous in this region.

The term "nuclear remodeling" refers to the artificial alteration of the molecular composition of the nuclear lamina or the chromatin of a cell.

The term "permeabilization" refers to the modification of the plasma membrane of a cell such that there is a formation of pores enlarged or generated in it or a partial or complete removal of the plasma membrane.

The term "pluripotent" refers to the characteristic of a stem cell that said stem cell is capable of differentiating into a multitude of differentiated cell types.

The term "totipotent" refers to the characteristic of a stem cell that said stem cell is capable of differentiating into any cell type in the body.

The term "undifferentiated cell" refers to an oocyte, an undifferentiated cell such as an ES, EG, ICM, ED, EC, teratocarcinoma cell, blastomere, morula, or germ-line cell.

Throughout this specification and claims, the word "comprise," or variations such as "comprises" or "comprising", will be understood to imply the inclusion of a stated integer or group of integers but not the exclusion of any other integer or group of integers.

Further, unless otherwise required by context, singular terms shall include pluralities and plural terms shall include the singular.

Unless otherwise defined, all technical and scientific terms used herein have the same meaning as commonly understood by one of ordinary skill in the art. In case of conflict, the present specification, including definitions, will control.

All publications, patents, patent publications and other references mentioned herein are incorporated by reference in their entirety.

Step 1: Nuclear Remodeling

The present invention utilizes a three-step process to improve the efficiency of reprogramming differentiated cells to an undifferentiated state.

In the first step, designated the nuclear remodeling step, the nuclear envelope and the chromatin of a differentiated cell are remodeled to more closely resemble the molecular composition of the nuclear envelope and chromatin, respectively, of an undifferentiated or a germ-line cell. This remodeling step can be performed in numerous ways, but the unique and nonobvious feature of this invention is that this remodeling step is performed in a separate step from the transfer of the remodeled genome into a cytoplast; further, the cytoplast is a cytoplast that is readily available, such as nonhuman animal oocyte cytoplasts or cytoplasts prepared from embryonal carcinoma (EC) cell lines, including EC cell lines genetically modified to make extracts and cytoplasts with improved capacity to reprogram under the present invention and that will then yield the final proliferating cell types. The remodeling of the somatic cell nucleus could be performed by transferring the nucleus into an oocyte of the same species (though differing in genotype from that somatic cell) or into an oocyte of a different species such as fish or amphibian (e.g. *Xenopus*) oocyte or egg, or in dispersed extracts from cells capable of reconstituting an undifferentiated or germ-line nuclear envelope around what was originally a genome from a differentiated cell.

Separating the nuclear remodeling step from the cellular reconstitution step solves problems inherent in existing reprogramming technologies. If nuclear remodeling is performed in one step separate from the step of cellular reconstitution to generate cells capable of proliferation, then it is possible to eliminate a dependence on oocytes of the same species as the differentiated cell and increase efficiency.

In the case of SCNT, the oocyte is a relatively large cell and as a result when a differentiated cell is transferred into a metaphase II oocyte, the ensuing breakdown of the nuclear envelope and chromosome condensation, and reassembly of the nuclear envelope largely from egg cell-derived components, results in the formation of a remodeled nuclear envelope as well as the impartation of nuclear regulatory factors, such as transcription factors, useful in reprogramming the chromatin. If the egg cell is activated at about the time of nuclear transfer, cell division may also occur, resulting in an embryo capable of giving rise to a culture of ES cells. The problems inherent in nuclear transfer, however, are that despite the relatively large volume of the oocyte and the incorporation of oocyte cell nuclear components into the reconstructed cell, nuclear transfer requires mircromanipulation, which is a highly-skilled procedure, as well as serial production using one cell at a time. Further, nuclear transfer is limited by the number of oocytes available. In the present invention, these difficulties are addressed by utilizing alternative nuclear remodeling technologies that, although requiring more than one step to obtain intact cells capable of cell division, nevertheless allow easy access to cytoplasm and are capable of remodeling a nucleus. Furthermore, these alternative techniques allow the simultaneous remodeling of many nuclei or genomes.

One modality for performing the first step of nuclear remodeling is through the use of fish or amphibian oocytes. The oocytes or eggs from the species *Xenopus laevis* have the advantage that they are widely studied, though most other oocytes or eggs from vertebrate species will function in a similar manner with the exception of egg cells with a large amount of yolk. While *Xenopus* oocytes are only marginally useful in reprogramming the chromatin of mammalian differentiated cell nuclei (Byrne et al., Curr Biol 13:1206-1213, (2003)), they can be used to nearly completely reassemble a germ-line nuclear envelope around a large number of differentiated somatic cells. Using *Xenopus* oocytes or *Xenopus* oocyte extract, the nuclear envelope and chromatin of the somatic cell is remodeled in the presence of such undifferentiated or germ-line proteins through a variety of means, including the injection of one or more intact or permeabilized differentiated cells into the oocyte, or the injection of isolated nuclei from said cells, into an oocyte. Further, other undifferentiated protein or other factors may be added to the oocytes or oocyte extract, or oocytes may be modified to express such additional factors that facilitate nuclear remodeling.

The differentiated cell that is reprogrammed may be any differentiated cell of a vertebrate species such as human, canine, equine, or feline somatic cells including fibroblasts, keratinocytes, lymphocytes, monocytes, epithelial cells, hematopoietic cells, or other cells.

One protocol for remodeling the nuclear envelope of these differentiated cells using oocytes from another species, such as *Xenopus* oocytes, is to inject permeabilized differentiated cells into interphase *Xenopus* oocytes, thereby allowing multiple differentiated cell nuclear envelopes to be remodeled over a period of several days. *Xenopus* oocytes from anesthetized mature females are surgically removed in MBS (magnesium buffered saline) and inspected for quality as is well-known in the art (Gurdon, Methods Cell Biol 16:125-139, (1977)). The oocytes are then washed twice in MBS and stored overnight at 14° C. in MBS. The next day, good quality stage V or VI oocytes are selected (Dumont, J. Morphol. 136:153-179, (1972)) and follicular cells are removed under a dissecting microscope in MBS. After defolliculation, the oocytes are stored again at 14° C. overnight in MBS with 1 µg/mL gentamycin (Sigma). The next day, oocytes with a healthy morphology are washed again in MBS and stored in MBS at 14° C. until use that day. The differentiated cells are then permeabilized by a permeabilization agent, such as Streptolysin O (SLO) or digitonin (Chan & Gurdon, Int. J. Dev. Biol. 40:441-451, (1996); Adam et al., Methods Enzymol. 219:97-110, (1992)). Approximately $1 \times 10^4$ differentiated cells are permeabilized, and suspended in ice-cold lysis buffer [$1 \times Ca^{2+}$-free MBS containing 10 mM EGTA (Gurdon, (1977)]. SLO (Wellcome diagnostics) is added at a final concentration of 0.5 units/mL. The suspension is maintained on ice for 7 minutes, then four volumes of $1 \times Ca^{2+}$-free MBS containing 1% bovine serum albumin (Sigma) is added. Aliquots of the cells may then be removed, diluted 1× in $1 \times Ca^{2+}$-free MBS containing 1% bovine serum albumin, and incubated at room temperature for five minutes to activate permeabilization. The cells are then placed back on ice for transfer into the *Xenopus* oocytes. The permeabilized cells are then transferred into *Xenopus* oocytes as is well known in the art (Gurdon, J. Embryol. Exp. Morphol. 36:523-540, (1976). Briefly, oocytes prepared as described above are placed on agar in high salt MBS (Gurdon, J. Embryol. Exp. Morphol. 36:523-540, (1976)). The DNA in the egg cells is inactivated by UV as described (Gurdon, Methods in Cell Biol 16:125-139, 1977) with the exception that the second exposure to the Hanovia UV source is not performed. Briefly, egg cells are placed on a glass slide with the animal pole facing up and are exposed to a Mineralite UV lamp for 1 minute to inactivate the female germinal vesicle. The permeabilized differentiated cells are taken up serially into a transplantation pipette 3-5 times the diameter of the cells and injected into the oocyte, preferably aiming toward the inactivated pronucleus. The egg containing the nuclei are incubated for one hour to 7 days and the nuclei are then removed and cryopreserved or used immediately in step two to reconstitute cells capable of proliferation.

Another manner in which the nuclear envelope and chromatin are remodeled is in cell-free extracts capable of forming nuclear envelopes from naked DNA or chromatin. Techniques for assembling nuclear envelopes around DNA or chromatin are known in the art (Marshall & Wilson, Trends in Cell Biol 7:69-74, (1997)). Such extracts may be isolated, for example, from *Xenopus* oocytes as is well-known in the art (Lohka, Cell Biol Int. Rep. 12:833-848 (1988)). Alternatively, extracts from undifferentiated cells of the same species may be used such as MII oocytes, oocytes at other stages of development, ES cells, EC cells, EG cells, or other cells in a relatively undifferentiated state. EC cells provide the advantage that they can be easily propagated in large quantities and human rather than nonhuman EC cells lessen concerns over the transmission of uncharacterized pathogens. Nonlimiting examples of such human EC cells include NTera-2, NTera-2 Cl. D1, NCCIT, Cates-1B, Tera-1, AND TERA-2 and nonlimiting examples of murine EC lines include MPRO, EML, F9, F19, D1 ORL UVA, NFPE, NF-1, and PFHR9. EC lines are readily obtained from sources such as the American Type Culture Collection and are grown at 37° C. in monolayer culture in medium characterized for that cell type and readily available on the internet, (http://stemcells.atcc.org) (complete medium).

In certain embodiments of the invention, the genome of the remodeled nucleus may be modified. Such modifications include, but are not limited to, the correction of mutations affecting disease, and other genetic modifications that alleviate disease symptoms or causes (e.g., in genes that would otherwise be targeted or used in gene-therapy). The nucleus being remodeled in step one may be modified by the addition of extracts from cells such as DT40 known to have a high level of homologous recombination. The addition of DNA targeting constructs and the extracts from cells permissive for a high level of homologous recombination will then yield cells after reconstitution in step 2 and screening in step 3 that have a desired genetic modification. For example, in certain embodiments, reprogrammed cells may be used to generate cells or tissues for cell-based therapies and/or transplantation.

In other embodiments of the invention, one or more factors are expressed or overexpressed in the undifferentiated cells (for example, in EC cells) used to obtain the nuclear remodeling extract or one or more factors may be added to the undifferentiated cells. Such factors include, for example, SOX2, NANOG, cMYC, OCT4, DNMT3B, embryonic histones, as well as other factors listed in Table 1 and their non-human counterparts. Increased expression of these factors may confer characteristics of an undifferentiated cell to the somatic cell nuclei and/or remove differentiated cell factors, thereby improving the frequency of reprogramming. Accordingly the invention also includes adding, expressing or over-expressing any other proteins that confer characteristics of an undifferentiated cell. In addition to the proteins mentioned above, the present invention includes other factors (such as transcriptional regulators and regulatory RNA) that induce or increase the expression of proteins expressed in undifferentiated cells and that improve the frequency of reprogramming. Further, any combinations of the above-mentioned factors may be used. For example, undifferentiated cells of the present invention may be modified to have increased expression of two, three, four, or more of any of the factors listed in Table 1. Likewise, two, three, four, or more of any of the factors listed in Table 1 may be added to the remodeling extract.

In other embodiments of the invention, the level of one or more factors in the undifferentiated cells used to obtain the nuclear remodeling extract is decreased relative to the levels found in unmodified cells. Such decreases in the level of a cell factor may be achieved by known methods, such as, for example, by use of transcriptional regulators, regulatory RNA, or antibodies specific for the cell factor.

In certain embodiments, gene constructs encoding the proteins listed in Table 1 or other factors, or regulatory proteins or RNAs that induce expression of these factors, are transfected into the cells by standard techniques. Such techniques include viral infection (e.g., lentivirus, papilloma virus, adenovirus, etc.) and transfection of plasmid and other vectors by chemical transfection (e.g., via calcium phosphate, lipids, dendrimers, etc.), electroporation, and microinjection. Alternatively, constructs that target the factors' endogenous promoters may be used to induce or increase expression of the factors. Other embodiments may use artificial chromosomes comprising one or more of these factors. In additional embodiments, chromosome mediated gene transfer or cell fusion/microcell fusion are used to introduce these factors into an undifferentiated cell. In other embodiments, homologous recombination to modify gene regulatory sequences can achieve increased expression of one or more of these factors.

In some embodiments, a transgene encoding the cell factor of interest may be delivered to the cell by pronuclear microinjection of DNA that is coated with recombinase. See, for example, Maga et al., Transgenic Research 12:485-496 (2003). Other known methods to improve the efficiency of generating transgenic cells may likewise be useful for purposes of this invention. Alternatively, the oocytes and/or undifferentiated cell extracts of the present invention may be obtained from transgenic animals that express human reprogramming factors (such as the factors listed in Table 1). For example, transgenic animals are generated using expression constructs carrying one or more of the genes listed in Table 1.

In some embodiments, the cell factors, or agents that alter the intracellular levels of the cell factors, may be introduced into undifferentiated cells by direct intracellular delivery. For example, the factors may be delivered using protein transduction domains or cell penetrating peptides, such as, for example, polyarginine. See Noguchi et al., Acta Med. Okayama 60:1-11 (2006). Cells into which the factors have been introduced may thus be useful in the above methods for nuclear remodeling.

In alternative embodiments, undifferentiated cell factors (such as the proteins and protein equivalents listed in Table 1), or agents that affect the levels of the cell factors, are introduced directly to the nuclear remodeling extract. In certain embodiments, recombinant proteins are added to the extract to improve the reprogramming efficiency.

The differentiated cells that may be effectively reprogrammed using the present invention include differentiated cells of any kind from any vertebrate (including human), including without limitation skin fibroblasts, keratinocytes, mucosal epithelial cells, or peripheral nucleated blood cells, using the following steps.

Preparation of Nuclear Remodeling Extract

Extracts from germ-line cells, such as ES, EG, or EC cells including but not limited to NTera-2 cells, are prepared in the prometaphase as is known in the art (Burke & Gerace, Cell 44: 639-652, (1986)). Briefly, after two days and while still in a log growth state, the medium is replaced with 100 mL of complete medium containing 2 mM thymidine (which sequesters the cells in S phase). After 11 hours, the cells are rinsed once with 25 mL of complete medium, then incubated with 75 mL of complete medium for four hours, at which point nocodazole is added to a final concentration of 600 ng/mL from 10,000× stock solution in DMSO. After one hour, loosely-attached cells are removed by mitotic shakeoff (Tobey et al., J. Cell Physiol. 70:63-68, (1967)). This first collection of removed cells is discarded, the medium is replaced with 50 mL of complete medium also containing 600 ng/mL of nocodazole. Prometaphase cells are then collected by shakeoff 2-2.5 hours later. The collected cells are then incubated at 37° C. for 45 minutes in 20 mL of complete medium containing 600 ng/mL nocodazole and 20 µM cytochalasin B. Following this incubation, the cells are washed twice with ice-cold Dulbecco's PBS, then once in KHM (78 mM KCl, 50 mM Hepes-KOH [pH 7.0], 4.0 mM $MgCl_2$, 10 mM EGTA, 8.37 mM $CaCl_2$, 1 mM DTT, 20 µM cytochlasin B). The cells are then centrifuged at 1000 g for five minutes, the supernatant discarded, and the cells are resuspended in the original volume of KHM. The cells are then homogenized in a dounce homogenizer on ice with about 25 strokes and progress determined by microscopic observation. When at least 95% of the cells are homogenized extracts held on ice for use in envelope reassembly or cryopreserved as is well known in the art.

Preparation of Condensed Chromatin from Differentiated Cells

Donor differentiated cells are exposed to conditions that remove the plasma membrane, resulting in the isolation of nuclei. These nuclei, in turn, are exposed to cell extracts that result in nuclear envelope dissolution and chromatin condensation. This dissolution and condensation results in the release of chromatin factors such as RNA, nuclear envelope proteins, and transcriptional regulators such as transcription factors that are deleterious to the reprogramming process. Differentiated cells are cultured in appropriate culture medium until they reach confluence. $1\times10^6$ cells are then harvested by trypsinization as is well known in the art, the trypsin is inactivated, and the cells are suspended in 50 mL of phosphate buffered saline (PBS), pelleted by centrifuging the cells at 500 g for 10 minutes at 4° C., the PBS is discarded, and the cells are placed in 50× the volume of the pellet in ice-cold PBS, and centrifuged as above. Following this centrifugation, the supernatant is discarded and the pellet is resuspended in 50× the volume of the pellet of hypotonic buffer (10 mM HEPES, pH 7.5, 2 mM $MgCl_2$, 25 mM KCl, 1 mM DTT, 10 μM aprotinin, 10 μM leupeptin, 10 μM pepstatin A, 10 μM soybean trypsin inhibitor, and 100 μM PMSF) and again centrifuged at 500 g for 10 min at 4° C. The supernatant is discarded and 20× the volume of the pellet of hypotonic buffer is added and the cells are carefully resuspended and incubated on ice for an hour. The cells are then physically lysed using procedures well-known in the art. Briefly, 5 ml of the cell suspension is placed in a glass Dounce homogenizer and homogenized with 20 strokes. Cell lysis is monitored microscopically to observe the point where isolated and yet undamaged nuclei result. Sucrose is added to make a final concentration of 250 mM sucrose (⅛ volume of 2 M stock solution in hypotonic buffer). The solution is carefully mixed by gentle inversion and then centrifuged at 400 g at 4° C. for 30 minutes. The supernatant is discarded and the nuclei are then gently resuspended in 20 volumes of nuclear buffer (10 mM HEPES, pH 7.5, 2 mM $MgCl_2$, 250 mM sucrose, 25 mM KCl, 1 mM DTT, 10 μM aprotinin, 10 μM leupeptin, 10 μM pepstatin A, 10 μM soybean trypsin inhibitor, and 100 μM PMSF). The nuclei are re-centrifuged as above and resuspended in 2× the volume of the pellet in nuclear buffer. The resulting nuclei may then be used directly in nuclear remodeling as described below or cryopreserved for future use.

Preparation of Condensation Extract

The condensation extract, when added to the isolated differentiated cell nuclei, will result in nuclear envelope breakdown and the condensation of chromatin. Because the purpose of step 1 is to remodel the nuclear components of a somatic differentiated cell with that of an undifferentiated cell, the condensation extract used is from undifferentiated cells which may or may not be also be the cells used to derive the extract for nuclear envelope reconstitution above. This results in a dilution of the components from the differentiated cell in extracts which contain the corresponding components desirable in reprogramming cells to an undifferentiated state. Germ-line cells such as ES, EG, or EC cells such as NTera-2 cl. D1 cells are easily obtained from sources such as the American Type Culture Collection and are grown at 37° C. in monolayer culture in appropriate medium (complete medium). While in a log growth state, the cells are plated at $5\times10^6$ cells per sq cm tissue culture flask in 200 mL of complete medium. Methods of obtaining extracts capable of inducing nuclear envelope breakdown and chromosome condensation are well known in the art (Collas et al., J. Cell Biol. 147:1167-1180, (1999)). Briefly, the germ-line cells in log growth as described above are synchronized in mitosis by incubation in 1 μg/ml nocodazole for 20 hours. The cells that are in the mitotic phase of the cell cycle are detached by mitotic shakeoff. The harvested detached cells are centrifuged at 500 g for 10 minutes at 4° C. Cells are resuspended in 50 ml of cold PBS, and centrifuged at 500 g for an additional 10 min. at 4° C. This PBS washing step is repeated once more. The cell pellet is then resuspended in 20 volumes of ice-cold cell lysis buffer (20 mM HEPES, pH 8.2, 5 mM $MgCl_2$, 10 mM EDTA, 1 mM DTT, 10 μM aprotinin, 10 μM leupeptin, 10 μM pepstatin A, 10 μM soybean trypsin inhibitor, 100 μM PMSF, and 20 μg/ml cytochalasin B, and the cells are centrifuged at 800 g for 10 minutes at 4° C. The supernatant is discarded, and the cell pellet is carefully resuspended in one volume of cell lysis buffer. The cells are placed on ice for one hour then lysed with a Dounce homogenizer. Progress is monitored by microscopic analysis until over 90% of cells and cell nuclei are lysed. The resulting lysate is centrifuged at 15,000 g for 15 minutes at 4° C. The tubes are then removed and immediately placed on ice. The supernatant is gently removed using a small caliber pipette tip, and the supernatant from several tubes is pooled on ice. If not used immediately, the extracts are immediately flash-frozen on liquid nitrogen and stored at −80° C. until use. The cell extract is then placed in an ultracentrifuge tube and centrifuged at 200,000 g for three hours at 4° C. to sediment nuclear membrane vesicles. The supernatant is then gently removed and placed in a tube on ice and used immediately to prepare condensed chromatin or cryopreserved as described above.

Methods of Use of Condensation Extract

If beginning with a frozen aliquot on condensation extract, the frozen extract is thawed on ice. Then an ATP-generating system is added to the extract such that the final concentrations are 1 mM ATP, 10 mM creatine phosphate, and 25 μg/ml creatine kinase. The nuclei isolated from the differentiated cells as described above are then added to the extract at 2,000 nuclei per 10 μl of extract, mixed gently, the incubated in a 37° C. water bath. The tube is removed occasionally to gently resuspend the cells by tapping on the tube. Extracts and cell sources vary in times for nuclear envelope breakdown and chromosome condensation. The progress is therefore monitored by periodic monitoring samples microscopically. When the majority of cells have lost their nuclear envelope and there is evidence of the beginning of chromosome condensation, the extract containing the condensing chromosome masses is placed in a centrifuge tube with an equal volume of 1 M sucrose solution in nuclear buffer. The chromatin masses are sedimented by centrifugation at 1,000 g for 20 minutes at 4° C. The supernatant is discarded, and the chromatin masses are gently resuspended in nuclear remodeling extract derived above. The sample is then incubated in a water bath at 33° C. for up to two hours and periodically monitored microscopically for formation of remodeled nuclear envelopes around the condensed and remodeled chromatin as described (Burke & Gerace, Cell 44:639-652, (1986). Once a large percentage of chromatin has been encapsulated in nuclear envelopes, the remodeled nuclei may be used in cellular reconstitution using any of the techniques described below in step 2.

Step 2—Cellular Reconstitution

Step 2, also referred to as "cellular reconstitution" in the present invention, is carried out using nuclei or chromatin remodeled by any of the techniques described in the present invention, such as in Examples 1 and 2 or combinations of the techniques described in Examples 1 and 2 as described more fully in the present invention.

One manner of performing step 2 using nuclei remodeled in step 1 of the present invention is to fuse the remodeled nuclei with enucleated cytoplasts of germ-line cells such as blastomeres, morula cells, inner cell mass cells, ES cells (including hES cells, EG cells, and EC cells) as is known in the art (Do & Scholer, Stem Cells 22:941-949 (2004)). Briefly, the human ES Cells are cultured under standard conditions (Klimanskaya et al. Lancet 365: 4997 (1995)). The cytoplasmic volume of the cells is increased by adding 10 µM cytochalasin B for 20 hours prior to manipulation. Cytoplasts are prepared by centrifuging trypsinized cells through a Ficoll density gradient using a stock solution of autoclaved 50% (wt/vol) Ficoll-400 solution in water. The stock Ficoll 400 solution is diluted in DMEM and with a final concentration of 10 µM cytochalasin B. The cells are centrifuged through a gradient of 30%, 25%, 22%, 18%, and 15% Ficoll-400 solution at 36° C. Layered on top is 0.5 mL of 12.5% Ficoll-400 solution with $10 \times 10^6$ ES cells. The cells are centrifuged at 40,000 rpm at 36° C. in an MLS-50 rotor for 30 minutes. The cytoplasts are collected from the 15% and 18% gradient regions marked on the tubes, rinsed in PBS, and mixed on a 1:1 ratio with remodeled nuclei from step one of the present invention or cryopreserved. Fusion of the cytoplasts with the nuclei is performed using a number of techniques known in the art, including polyethylene glycol (see Pontecorvo "Polyethylene Glycol (PEG) in the Production of Mammalian Somatic Cell Hybrids" Cytogenet Cell Genet. 16(1-5):399-400 (1976)), the direct injection of nuclei, sedai viral-mediated fusion, or other techniques known in the art. The cytoplasts and the nuclei are placed briefly in 1 mL of prewarmed 50% polyethylene glycol 1500 (Roche) for one minute. 20 mL of DMEM was then added over a five minute period to slowly remove the polyethylene glycol. The cells are centrifuged once at 130 g for five minutes and then taken back up in 50 µL of ES cell culture medium and placed beneath a feeder layer of fibroblasts under conditions to promote the outgrowth of an ES cell colony.

Another technique for performing step 2, also referred to as "cellular reconstitution" in the present invention, is to fuse the remodeled nuclei with anucleate cytoplasmic blebs of germ-line cells, such as hES cells, attached to a physical substrate as is well known in the art (Wright & Hayflick, Exp. Cell Res. 96:113-121, (1975); & Wright & Hayflick, Proc. Natl. Acad. Sci., USA, 72:1812-1816, (1975). Briefly, the cytoplasmic volume of the germ-line cells is increased by adding 10 µM cytochalasin B for 20 hours prior to manipulation. The cells are then trypsinized and replated on sterile 18 mm coverslips, cylinders, or other physical substrate coated with material promoting attachment. The cells are plated at a density such that after an overnight incubation at 37° C. and one gentle wash with medium, the cells cover a portion, preferably about 90%, of the surface area of the coverslip or other substrate. The substrates are then placed in a centrifuge tube in a position such that centrifugation will result in the removal of the nuclei from the cytoplast containing 8 mL of 10% Ficoll-400 solution and centrifuged at 20,000 g at 36° C. for 60 minutes. Remodeled nuclei resulting from step one of the present invention are then spread onto the coverslip or substrate with a density of at least that of the cytoplasts, preferable at least five times the density of the cytoplasts. Fusion of the cytoplasts with the nuclei is performed using polyethylene glycol (see Pontecorvo "Polyethylene Glycol (PEG) in the Production of Mammalian Somatic Cell Hybrids" Cytogenet Cell Genet. 16(1-5):399-400 (1976). Briefly, in 1 mL of prewarmed 50% polyethylene glycol 1500 (Roche) in culture medium is placed over the coverslip or substrate for one minute. 20 mL of culture medium is then added drip-wise over a five minute period to slowly remove the polyethylene glycol. The entire media is then aspirated and replaced with culture medium. Techniques other than centrifugation such as vibration or physical removal of the nuclei using a micropipette may also be used.

In certain embodiments of the present invention, the undifferentiated cells used in step 2 may first be manipulated to express or overexpress factors such as, for example, SOX2, NANOG, cMYC, OCT4, DNMT3B, any other factors listed in Table 1 and their non-human homologues, and/or other factors (e.g., regulatory RNA or constructs targeting the promoters of the genes listed in Table 1 and their non-human homologues) that confer undifferentiated cell behavior and facilitate reprogramming. Constructs encoding such factors may be transfected into undifferentiated cells, such as germ-line cells (e.g., blastomeres, morula cells, inner cell mass cells, ES cells, including hES cells, EG cells, or EC cells), by standard techniques known in the art. Examples of manipulating undifferentiated cells to express cellular factors are described above in Step 1. In alternative embodiments, such factors are introduced into the undifferentiated cells by injection or other methods. Examples of such methods to manipulate undifferentiated cells are likewise described above in Step 1.

In alternative embodiments of the present invention, nuclear envelope reconstitution occurs following homologous recombination reactions that have modified target chromosomes. Thus, in one embodiment, as an optional step following nuclear envelope breakdown and chromatin condensation but before nuclear envelope reconstitution, DT40 extracts, or other recombination-proficient extracts or protein preparations, are added to the condensed chromosomes along with DNA targeting constructs such that recombination will result in the replacement of one or more genomic DNA sequences with the sequence(s) provided in the constructs. Exemplary embodiments of such methods are provided in Examples 3, 4, 5, and 6.

Step 3—Analysis of the Karyotype and Extent of Reprogramming

Cells reconstituted following steps 1 and 2 of the present invention can be characterized to determine the pattern of gene expression and whether the reprogrammed cells display a pattern of gene expression similar to the expression pattern expected of undifferentiated cells such as ES cell lines using techniques well known in the art including transcriptomics (Klimanskaya et al., Cloning and Stem Cells, 6(3): 217-245 (2004)). Karyotypic analysis may be performed by means of chromosome spreads from mitotic cells, spectral karyotyping, assays of telomere length, total genomic hybridization, or other techniques well known in the art. In the case where the karyotype is normal, but telomere length or the extent of reprogramming is not complete, the cells may be used as nuclear donors and steps 1 and 2 repeated any number of times.

For example, the gene expression pattern of the reprogrammed cells may be compared to the gene expression pattern of embryonic stem cells or other undifferentiated cells. If the gene expression patterns are not similar, then the reprogrammed cell may be used in subsequent reprogramming steps until its gene expression is similar to the expression pattern of an undifferentiated cell (e.g., embryonic stem cell). The undifferentiated or embryonic stem cell to which the reprogrammed cell is compared may be from the same species as the donor differentiated somatic cell; alternatively, the undifferentiated or embryonic stem cell to which the reprogrammed cell is compared may be from the same species as the cytoplast or cytoplasmic bleb used in step 2. In some embodiments, a similarity in gene expression pattern exists between a reprogrammed cell and an undifferentiated cell (e.g., embryonic stem cell) if certain genes expressed in an undifferentiated cell are also expressed in the reprogrammed cell. For example, certain genes (e.g., telomerase) that are typically undetectable in differentiated somatic cells may be used to monitor the extent of reprogramming. Likewise, for certain genes, the absence of expression may be used to assess the extent of reprogramming. In certain embodiments, a cell may be considered reprogrammed if it expresses (1) E-cadherin (for human cells, CDH1; Accession No. NM_004360.2) mRNA at levels of at least 5% of the expression level of the housekeeping gene GAPD (for human cells, NM_002046.2) (data not shown); (2) detectable telomerase reverse transcriptase mRNA or exhibits telomerase activity as assessed by the TRAP assay (TRAPeze); and (2) LIN28 (NM_024674.3; or its non-human equivalent for non-human cells) at levels of at least 5% of the housekeeping gene GAPD (for human cells, NM_002046.2)(data not shown).

Other examples of the ways the different means of performing steps 1 and 2 of the present invention can be combined include permeabilizing somatic cells by SLO, resealing the cells, and isolating the resulting partially-remodeled nuclei and then using the nuclei in the cellular reconstitution of step two. Also, the remodeled chromatin obtained by isolating differentiated cell nuclei, then exposing the nuclei to extracts from cells in the mitotic phase of the cell cycle to cause nuclear envelope breakdown and chromatin condensation, may then be transferred into the cytoplast of an ES cell, EC cell, or EG cell without reforming the nuclear envelope prior to cellular reconstitution. In addition, the somatic differentiated cell may be permeabilized as described above and exposed to extracts from oocytes or germ-line cells. The condensed chromatin from such cells may then be obtained, and then that chromatin may be fused with the recipient cytoplasts to yield reprogrammed cells. The fusion of chromatin with the cytoplasts is achieved by microinjection or is aided by fusigenic compounds as is known in the art (see, for example, U.S. Pat. Nos. 4,994,384 and 5,945,577). The fusigenic reagents include, but are not limited to, polyethylene glycol (PEG), lipophilic compounds such as Lipofectin®, Lipofectamin®, DOTAP®, DOSPA®, or DOPE® For insertion of the chromatin into the cytoplasts, the coated chromatin is placed next to the cytoplast membrane and the complexes are maintained at a temperature of 20-30° C. and monitored using a microscope. Once fusion has occurred, the medium is replaced with culture medium for the cultivation of undifferentiated cells and in culture conditions that promote the growth of said undifferentiated cells.

The cellular factors and methods of use listed herein may be used in alternative reprogramming techniques, such as in the methods disclosed by Callas and Robl, U.S. patent application Ser. No. 10/910,156, which is incorporated herein by reference in its entirety. The factors may, for example, be added to media (or alternatively expressed in cells used to obtain extract media) used to incubate a nucleus or chromatin mass from a donor cell under conditions that allow nuclear or cytoplasmic components from an undifferentiated cell to be added to the donor nucleus or chromatin mass.

The in vitro remodeling of somatic cell-derived DNA in step one of the present invention is utilized as a model of reprogramming of a somatic cell and an assay useful in analyzing the molecular mechanisms of reprogramming. The selective addition, alteration, removal, or sequestration of particular molecular components, and the subsequent scoring of the extent of reprogramming or the extent of activation of telomerase and extension of telomere length allow the characterization of the role of particular molecules in the reprogramming that occurs during SCNT. The critical molecules characterized in this application of the present invention are then used by their corresponding addition or deletion (e.g., by their addition if they facilitate reprogramming, or by their deletion if they inhibit reprogramming). Deletion can be achieved by, for instance, immune depletion, in oocytes or reprogramming extracts used in step one. Specific molecular alterations can be introduced by techniques well known in the art, including but not limited to, the addition of protein components, the removal of protein components such as by immunoprecipitation, the addition of other cellular components such as lipids, ions, DNA, or RNA. RNA may be prepared from oocytes, blastomeres, morula cells, ICM cells, ED cells or germ-line cells such as ES, EG, or EC cells. Total or fractions of the RNA such as microRNA are prepared as is well known in the art. This "germ-line RNA" is then introduced into the permeabilized cells of Example 1 at the point of incubating the cells at room temperature in order to allow the RNA to diffuse into the cells and improve the reprogramming of the somatic cells to an embryonic state once transplanted into the oocyte.

A common feature of the present invention is that, regardless of which techniques are used to remodel the nuclear envelope and chromatin of a differentiated cell, at least two, and in some embodiments three, steps are used: one step wherein the chromatin and/or nuclear envelope are remodeled, a second step wherein the remodeled chromatin and/or nuclear envelope are reconstituted into a cytoplast to make a cell capable of cell division, and a third step wherein the resulting proliferating reprogrammed cells are analyzed to determine the degree of reprogramming and karyotype. If there is not a sufficient degree of reprogramming, the cells are cycled back to step one.

Somatic cells reprogrammed as described herein may be used to generate ES cells or ES cell lines including, but not limited to human ES cell lines. Since isolated human ES cells have a poor efficiency in generating cell lines, the reprogrammed cells of the present invention may be aggregated together to facilitate the generation of stable ES cell lines. Such aggregation may include plating the cells at high density, placing the cells in a depression in the culture dish such that gravity brings the cells into close proximity, or the cells can be co-cultured with feeder cells or with existing ES cell lines.

Human embryonic cells, e.g., human ES cells may be cultured on feeder cells, e.g., mouse embryonic fibroblasts, or human feeder cells such as fibroblasts (e.g., human foreskin fibroblasts, human skin fibroblasts, human endometrial fibroblasts, human oviductal fibroblasts) and placental cells. In one embodiment, the human feeder cells may be autologous feeder cells derived from the same culture of reprogrammed cells by direct differentiation and the clonal isolation of cells useful in ES cell derivation. The human embryonic cells are grown in ES cell medium or any medium that supports growth of the embryonic cells, e.g., Knockout DMEM (Invitrogen Cat #10829-018).

Alternatively, the reprogrammed cells obtained from the methods of the present invention may be co-cultured in juxtaposition with exiting ES cell lines. Exemplary human embryonic cells include, but are not limited to, embryonic stem cells, such as from already established lines, embryo carcinoma cells, murine embryonic fibroblasts, other embryo-like cells, cells of embryonic origin or cells derived from embryos, many of which are known in the art and available from the American Type Culture Collection, Manassas, Va. 20110-2209, USA, and other sources.

The embryonic cells may be added directly to the cultured reprogrammed cells or may be grown in close proximity to, but not in direct contact with, the cultured reprogrammed cells. The method comprises the step of directly or indirectly contacting the cultured reprogrammed cells with embryonic cells. Alternatively, the culture of reprogrammed cells and the culture of embryonic cells are indirectly connected or merged. This can be achieved by any method known in the art including, for example, using light mineral oil such as Cooper Surgical ACT# ART4008, paraffin oil or Squibb's oil. The connections can be made by using a glass capillary or similar device. Such indirect connections between the cultured reprogrammed cells and the embryonic cells allows gradual mixing of the embryo medium (in which the reprogrammed cells are cultured) and the ES cell medium (in which the human embryonic cells are grown).

In another embodiment, the reprogrammed cells may be co-cultured with a human embryo. For example, the reprogrammed cells are co-cultured with the embryo in a microdroplet culture system or other culture system known in the art, but which does not permit cell-cell contact but could permit cell-secreted factor and/or cell-matrix contact. The volume of the microdrop may be reduced, e.g., from 50 microliters to about 5 microliters to intensify the signal. In another embodiment the embryonic cells may be from a species other than human, e.g., non-human primate or mouse.

After about 3-4 days, the reprogrammed cells exhibit properties of ES cells. While not wishing to be bound by any particular theory, it is believed that over a period of days or weeks the cultured reprogrammed cells exhibit facilitated ES cell growth perhaps as a result of factors secreted by the human embryonic cells or by the extracellular matrix. The above-described methods for producing ES cells are described in application PCT/US05/39776, U.S. Ser. No. 11/267,555 and 60/831,698, which are incorporated herein in their entirety. Properties of ES cells or an ES cell line may include, without limitation, the expression of telomerase and/or telomerase activity, and the expression of one or more known ES cell markers.

In certain embodiments, the reprogrammed cell culture conditions may include contacting the cells with factors that can inhibit or otherwise potentiate the differentiation of the cells, e.g., prevent the differentiation of the cells into non-ES cells, trophectoderm or other cell types. Such conditions can include contacting the cultured cells with heparin or introducing reprogramming factors into the cells or extracts as described herein. In yet another embodiment, expression of cdx-2 is prevented by any means known in the art including, without limitation, introducing CDX-2 RNAi into the reprogrammed cells, thereby inhibiting differentiation of the reprogrammed cells into TS cells, thereby insuring that said cells could not lead to a competent embryo.

In another embodiment of the present invention, the reprogrammed cells resulting from steps 1 and 2 of the methods of this invention are directly used to produce differentiated progeny without the production of an ES cell line. Thus, in one aspect, the present invention provides a method for producing differentiated progenitor cells, comprising:
  (i) obtaining reprogrammed cells using steps 1-2 or 1-3 of the methods of this invention; and
  (ii) inducing differentiation of the reprogrammed cells to produce differentiated progenitor cells without producing an embryonic stem cell line.
The differentiated progenitor cells can be used to derive cells, tissues and/or organs which are advantageously used in the area of cell, tissue, and/or organ transplantation which include all of the cells and applications described herein for ES-derived cells and tissues.

In the past, long-term culture of inner cell mass cells was used to produce embryonic stem cell lines. Subsequently, the embryonic stem cells were cultured and conditionally genetically-modified, and induced to differentiate in order to produce cells to make cells for therapy. Co-owned pending U.S. pending application 2005/0265976A1 describes a method of producing differentiated progenitor cells from inner cell mass cells or morula-derived cells by directly inducing the differentiation of those cells without producing an embryonic stem cell line. The application also describes the use of said differentiated cells, tissues, and organs in transplantation therapy. In the method of the present invention, reprogrammed cells derived from steps 1-2 or 1-3 as described herein are induced to directly differentiate into differentiated progenitor cells which are then used for cell therapy and for the generation of cells, tissues, and organs for transplantation. If desired, genetic modifications can be introduced, for example, into somatic cells prior to reprogramming or into the chromatin in the extracts as described herein. Thus, the differentiated progenitor cells of the present invention do not possess the pluripotency of an embryonic stem cell, or an embryonic germ cell, and are, in essence, tissue-specific partially or fully differentiated cells. These differentiated progenitor cells may give rise to cells from any of three embryonic germ layers, i.e., endoderm, mesoderm, and ectoderm. For example, the differentiated progenitor cells may differentiate into bone, cartilage, smooth muscle, dermis with a prenatal pattern of gene expression and capable of promoting scarless wound repair, and hematopoietic or hemangioblast cells (mesoderm); definitive endoderm, liver, primitive gut, pancreatic beta cells, progenitors of pancreatic beta cells, and respiratory epithelium (endoderm); or neurons, glial cells, hair follicles, or eye cells including retinal neurons and retinal pigment epithelium using techniques known in the art, or using techniques described in the pending applications PCT/US2006/013573 filed Apr. 11, 2006, and U.S. Application No. 60/811,908, filed Jun. 7, 2006, which are both incorporated in their entirety by reference.

One advantage of the methods of the present invention is that the cells obtained by steps 1-2 or steps 1-3 can be differentiated without prior purification or establishment of a cell line. The cells obtained by the methods disclosed herein can be differentiated without the selection or purification of the cells. Accordingly in certain embodiments, a heterogeneous population of cells comprising reprogrammed cells are differentiated into a desired cell type. In one embodiment, a mixture cells obtained from steps 1-2 as described herein are exposed to one or more differentiation factors and cultured in vitro. Thus in certain embodiments, there is no need to purify the reprogrammed cells or to establish an ES or other cell line before differentiation. In one embodiment, a heterogeneous population of cells comprising reprogrammed cells is permeabilized to facilitate access to differentiation factors and subsequent differentiation.

Furthermore, it is not necessary for the differentiated progenitor cells of the present invention to express the catalytic component of telomerase (TERT) and be immortal, or that the progenitor cells express cell surface markers found on embryonic stem cells such as the cell surface markers characteristic of primate embryonic stem cells: positive for SSEA-3, SSEA-4, TRA-1-60, TRA-1-81, alkaline phosphatase activity, and negative for SSEA-1. More-over, the differentiated progenitor cells of the present invention may be distinct from embryoid bodies, i.e., embryoid bodies are derived from embryonic stem cells whereas the differentiated stem cells of the present invention may be derived from reprogrammed cells without the production of ES cell lines.

Applications

The cells resulting from steps 1 and 2 of the methods of this invention are plated in conditions that promote the growth of ES cells, such as hES cells, as is well known in the art. Briefly, the cells may be left on the substrate in which the enucleated cytoplasts are prepared, or they may be trypsinized and centrifuged at 700×g for 3 minutes and taken up into a sterile Pasteur pipette and placed under a feeder monolayer to concentrate and to co-localize the cells. The cells may be co-cultured with other vigorously-growing ES cell lines that can be easily removed by means such as suicide induction after encouraging the growth of the reprogrammed stem cells. The reprogrammed cells may also be concentrated into a small surface area of the growth surface by plating in a small cloning cylinder as well as be cultured by other techniques well known in the art.

In another aspect of the invention, the method comprises the utilization of cells derived from the reprogrammed cells of the present invention in research and in therapy. Such reprogrammed pluripotent or totipotent cells may be differentiated into any of the cells in the body including, without limitation, skin, cartilage, bone skeletal muscle, cardiac muscle, renal, hepatic, blood and blood forming, vascular precursor and vascular endothelial, pancreatic beta, neurons, glia, retinal, inner ear follicle, intestinal, lung, cells.

In a particular embodiment, the reprogrammed cells may be differentiated into cells with a dermatological prenatal pattern of gene expression that is highly elastogenic or capable of regeneration without causing scar formation. Dermal fibroblasts of mammalian fetal skin, especially corresponding to areas where the integument benefits from a high level of elasticity, such as in regions surrounding the joints, are responsible for synthesizing de novo the intricate architecture of elastic fibrils that function for many years without turnover. In addition, early embryonic skin is capable of regenerating without scar formation. Cells from this point in embryonic development made from the reprogrammed cells of the present invention are useful in promoting scarless regeneration of the skin including forming normal elastin architecture. This is particularly useful in treating the symptoms of the course of normal human aging, or in actinic skin damage, where there can be a profound elastolysis of the skin resulting in an aged appearance including sagging and wrinkling of the skin.

In another embodiment of the invention, the reprogrammed cells are exposed to inducers of differentiation to yield other therapeutically-useful cells such as retinal pigment epithelium, definitive endoderm, pancreatic beta cells and precursors to pancreatic beta cells, hematopoietic precursors and hemangioblastic progenitors, neurons, respiratory cells, muscle progenitors, cartilage and bone-forming cells, cells of the inner ear, neural crest cells and their derivatives, gastrointestinal cells, liver cells, kidney cells, smooth and cardiac muscle cells, dermal progenitors including those with a prenatal pattern of gene expression useful in promoting scarless wound repair, as well as many other useful cell types of the endoderm, mesoderm, and endoderm. Such inducers include but are not limited to: cytokines such as interleukin-alpha A, interferon-alpha A/D, interferon-beta, interferon-gamma, interferon-gamma-inducible protein-10, interleukin-1-17, keratinocyte growth factor, leptin, leukemia inhibitory factor, macrophage colony-stimulating factor, and macrophage inflammatory protein-1 alpha, 1-beta, 2, 3 alpha, 3 beta, and monocyte chemotactic protein 1-3, 6kine, activin A, amphiregulin, angiogenin, B-endothelial cell growth factor, beta cellulin, brain-derived neurotrophic factor, C10, cardiotrophin-1, ciliary neurotrophic factor, cytokine-induced neutrophil chemoattractant-1, eotaxin, epidermal growth factor, epithelial neutrophil activating peptide-78, erythropoietin, estrogen receptor-alpha, estrogen receptor-beta, fibroblast growth factor (acidic and basic), heparin, FLT-3/FLK-2 ligand, glial cell line-derived neurotrophic factor, Gly-His-Lys, granulocyte colony stimulating factor, granulocytemacrophage colony stimulating factor, GRO-alpha/MGSA, GRO-beta, GRO-gamma, HCC-1, heparin-binding epidermal growth factor, hepatocyte growth factor, heregulin-alpha, insulin, insulin growth factor binding protein-1, insulin-like growth factor binding protein-1, insulin-like growth factor, insulin-like growth factor II, nerve growth factor, neurotophin-3,4, oncostatin M, placenta growth factor, pleiotrophin, rantes, stem cell factor, stromal cell-derived factor 1B, thromopoietin, transforming growth factor-(alpha, beta 1, 2, 3, 4, 5), tumor necrosis factor (alpha and beta), vascular endothelial growth factors, and bone morphogenic proteins, enzymes that alter the expression of hormones and hormone antagonists such as 17B-estradiol, adrenocorticotropic hormone, adrenomedullin, alpha-melanocyte stimulating hormone, chorionic gonadotropin, corticosteroid-binding globulin, corticosterone, dexamethasone, estriol, follicle stimulating hormone, gastrin 1, glucagons, gonadotropin, L-3,3',5'-tri-iodothyronine, leutinizing hormone, L-thyroxine, melatonin, MZ-4, oxytocin, parathyroid hormone, PEC-60, pituitary growth hormone, progesterone, prolactin, secretin, sex hormone binding globulin, thyroid stimulating hormone, thyrotropin releasing factor, thyroxin-binding globulin, and vasopressin, extracellular matrix components such as fibronectin, proteolytic fragments of fibronectin, laminin, tenascin, thrombospondin, and proteoglycans such as aggrecan, heparan sulphate proteoglycan, chontroitin sulphate proteoglycan, and syndecan. Other inducers include cells or components derived from cells from defined tissues used to provide inductive signals to the differentiating cells derived from the reprogrammed cells of the present invention. Such inducer cells may derive from human, nonhuman mammal, or avian, such as specific pathogen-free (SPF) embryonic or adult cells.

Differentiated progeny may also be derived from reprogrammed ES cell lines or directly differentiated from reprogrammed cells using clonal isolation procedures as described in the pending application PCT/US2006/013573 filed Apr. 11, 2006, and U.S. Application No. 60/811,908, filed Jun. 7, 2006, which are incorporated my means of reference. Methods of differentiating reprogrammed cells obtained by the methods disclosed herein may comprise a step of permeabilization of the reprogrammed cell. For example, ES cell lines generated by the reprogramming techniques described herein, or alternatively a heterogeneous mixture of cells comprising reprogrammed cells, may be permeabilized before exposure to one or more differentiation factors or cell extract or other preparation comprising differentiation factors. Permeabilization techniques include, for example, incubation of cell(s) with a detergent, such as digitonin, or a bacterial toxin, such as Streptolysin O, or by methods as described in PCT/US2006/013573 filed Apr. 11, 2006, and U.S. Application No. 60/811,908, filed Jun. 7, 2006, which are incorporated my means of reference. In certain embodiments, reprogrammed cells are permeabilized and then exposed to extract from beta cells (e.g., bovine beta cells).

The methods of the present invention also enable the generation of cell lines homozygous or hemizygous for MHC antigens. Hemizygous or homozygous HLA cell lines may be generated in differentiated cell lines that are dedifferentiated to generate a totipotent or pluripotent stem cell line that is homozygous at the HLA locus. See for example U.S. Patent Publication No. US 2004/0091936, filed May 14, 2004, the disclosure of which is incorporated by reference herein. For instance, differentiated cells can be dedifferentiated using the reprogramming methods disclosed herein to generate a totipotent or pluripotent stem cell. Totipotent and pluripotent stem cells homozygous for histocompatibility antigens, e.g., MHC antigens, can be produced by remodeling the nucleus of a somatic cell homozygous for the antigens and then reconstituting the remodeled nucleus as described in the present disclosure. Cytoplasm from an undifferentiated cell may be added to isolated nuclei or chromatin from differentiated cells, or differentiated cells that are permeabilized. Following reprogramming of the somatic cell, the resulting dedifferentiated, pluripotent, stem or stem-like homozygous cell may be differentiated into a desired cell type. Methods for inducing re-differentiation into a cell type other than that of the initial differentiated cells are described, for example, in co-owned and co-pending U.S. publication 20030027330, filed Apr. 2, 2002, the disclosure of which is incorporated herein by reference in its entirety. Further, during step 1 of de-differentiation, the nucleus remodeled in step one may be modified by homologous recombination. The addition of extracts from cells such as DT40 known to have a high level of homologous recombination along with DNA targeting constructs will then yield cells after reconstitution in step 2 and screening in step 3 that have a desired genetic modification and that are homozygous for MHC antigen.

Many of the steps in the present invention are time intensive and require skilled technicians to perform the steps at a high level of quality. To decrease cost and increase quality and reproducibility, many of the steps described above can be automated through the use of robotics. Robotic platforms can, for example, culture cells, introduce buffers and other reagents, thaw and introduce extracts, and reconstitute cells in step 2.

The present invention is commercialized by regional centers that receive differentiated cells from animals or humans in need of cell therapy and perform steps 1-2 or 1-3 of the methods of the present invention, and return either the reprogrammed pluripotent stem cells to a clinical center where they are differentiated into a therapeutically-useful cell type, or the differentiation is performed in the regional center and the cells ready for transplantation are shipped in live cultures or in a cryopreserved state to the health care provider.

EXAMPLES

Example 1

Nuclear Remodeling

The first step (also referred to herein as the "nuclear reprogramming step") is performed using human peripheral blood mononuclear cells which are purified from blood using Ficoll gradient centrifugation to yield a buffy coat comprised primarily of lymphocytes and monocytes as is well known in the art. The use of lymphocytes with a rearranged immunoglobulin locus as donors in the present invention will result in stem cells with the same rearranged loci. In the case where the desired outcome of the experiment is not cells with a preformed rearrangement in immunoglobulin genes, the monocytes are purified from the lymphocytes by flow cytometry as is well known in the art and stored at room temperature in Dulbecco's minimal essential medium (DMEM) or cryopreserved until use. *Xenopus* oocytes from MS222 anesthetized mature females are surgically removed in MBS buffer and inspected for quality as is well-known in the art (Gurdon, Methods Cell Biol 16:125-139, (1977)). The oocytes are then washed twice in MBS and stored overnight at 14° C. in MBS. The next day, good quality stage V or VI oocytes are selected (Dumont, J. Morphol. 136:153-179, (1972)) and follicular cells are removed under a dissecting microscope in MBS. After defolliculation, the oocytes are stored again at 14° C. overnight in MBS with 1 µg/mL gentamycin (Sigma). The next day, oocytes with a healthy morphology are washed again in MBS and stored in MBS at 14° C. until use that day. Approximately $1 \times 10^4$ monocytes are permeabilized by SLO treatment as described by Chan & Gurdon, Int. J. Dev. Biol. 40:441-451, (1996). Briefly, the cells are suspended in ice-cold lysis buffer [$1 \times Ca^{2+}$-free MBS containing 10 mM EGTA (Gurdon, (1977)]. SLO (Wellcome diagnostics) is added at a final concentration of 0.5 units/mL. The suspension is maintained on ice for 7 minutes, then four volumes of $1 \times Ca^{2+}$-free MBS containing 1% bovine serum albumin (Sigma) is added. Aliquots of the cells may then be removed, diluted $1 \times$ in $1 \times Ca^{2+}$-free MBS containing 1% bovine serum albumin, and incubated at room temperature for five minutes to activate permeabilization. The cells are then placed back on ice for transfer into the *Xenopus* oocytes. The permeabilized cells are then transferred into *Xenopus* oocytes as is well known in the art (Gurdon, J. Embryol. Exp. Morphol. 36:523-540, (1976). Briefly, oocytes prepared as described above are placed on agar in high salt MBS (Gurdon, J. Embryol. Exp. Morphol. 36:523-540, (1976)). The DNA in the egg cells is inactivated by UV as described (Gurdon, Methods in Cell Biol 16:125-139, 1977) with the exception that the second exposure to the Hanovia UV source is not performed. Briefly, egg cells are placed on a glass slide with the animal pole facing up and are exposed to a Mineralite UV lamp for 1 minute to inactivate the female germinal vesicle. The permeabilized monocytes are taken up serially into a transplantation pipette 3-5 times the diameter of the monocytes and injected into the oocyte, preferably aiming toward the inactivated pronucleus. The egg containing the nuclei are incubated for one hour to 7 days, preferably 7 days, then removed and used in step 2. The oocytes may, if desired, be manipulated prior to use to alter the levels of one or more cell factors as described above.

Example 2

Nuclear Remodeling

In this example, step one of nuclear remodeling is carried out in an extract from undifferentiated cells of the same species as the differentiated cell; human dermal fibroblasts nuclei are remodeled in vitro using mitotic cell extracts from the human embryonal carcinoma cell line NTera-2. However, extracts from cells of a different species may alternatively be used.

Preparation of Nuclear Remodeling Extract

NTera-2 cl. D1 cells are easily obtained from sources such as the American Type Culture Collection (CRL-1973) and are grown at 37° C. in monolayer culture in DMEM with 4 mM L-glutamine, 1.5 g/L sodium bicarbonate and 4.5 g/L glucose, 10% fetal bovine serum (complete medium). While in a log growth state, the cells are plated at $5 \times 10^6$ cells per sq cm tissue culture flask in 200 mL of complete medium. Extracts from cells in the prometaphase are prepared as is known in the art (Burke & Gerace, Cell 44: 639-652, (1986)). Briefly, after two days and while still in a log growth state, the medium is replaced with 100 mL of complete medium containing 2 mM thymidine (which sequesters the cells in S phase). After 11 hours, the cells are rinsed once with 25 mL of complete medium, then the cells are incubated with 75 mL of complete medium for four hours, at which point nocodazole is added to a final concentration of 600 ng/mL from 10,000× stock solution in DMSO. After one hour, loosely-attached cells are removed by mitotic shakeoff (Tobey et al., J. Cell Physiol. 70:63-68, (1967)). This first collection of removed cells is discarded, the medium is replaced with 50 mL of complete medium also containing 600 ng/mL of nocodazole. Prometaphase cells are then collected by shakeoff 2-2.5 hours later. The collected cells are then incubated at 37° C. for 45 minutes in 20 mL of complete medium containing 600 ng/mL nocodazole and 20 μM cytochalasin B. Following this incubation, the cells are washed twice with ice-cold Dulbecco's PBS, then once in KHM (78 mM KCl, 50 mM Hepes-KOH [pH 7.0], 4.0 mM $MgCl_2$, 10 mM EGTA, 8:37 mM $CaCl_2$, 1 mM DTT, 20 μM cytochlasin B). The cells are the centrifuged at 1000 g for five minutes, the supernatant discarded, and the cells are resuspended in the original volume of KHM. The cells are then homogenized in a dounce homogenizer on ice with about 25 strokes and progress determined by microscopic observation. When at least 95% of the cells are homogenized extracts held on ice for use in envelope reassembly or cryopreserved as is well known in the art.

Preparation of Condensed Chromatin from Differentiated Cells

Donor dermal fibroblasts will be exposed to conditions that remove the plasma membrane, resulting in the isolation of nuclei. These nuclei, in turn, will be exposed to cell extracts that result in nuclear envelope dissolution and chromatin condensation. This results in the release of chromatin factors such as RNA, nuclear envelope proteins, and transcriptional regulators such as transcription factors that are deleterious to the reprogramming process. Dermal fibroblasts are cultured in DMEM with 10% fetal calf serum until the cells reach confluence. $1 \times 10^6$ cells are then harvested by trypsinization as is well known in the art, the trypsin is inactivated, and the cells are suspended in 50 mL of phosphate buffered saline (PBS), pelleted by centrifuging the cells at 500 g for 10 minutes at 4° C., the PBS is discarded, and the cells are suspended in 50× the volume of the pellet in ice-cold PBS, and centrifuged as above. Following this centrifugation, the supernatant is discarded and the pellet is resuspended in 50× the volume of the pellet of hypotonic buffer (10 mM HEPES, pH 7.5, 2 mM $MgCl_2$, 25 mM KCl, 1 mM DTT, 10 μM aprotinin, 10 μM leupeptin, 10 μM pepstatin A, 10 μM soybean trypsin inhibitor, and 100 μM PMSF) and again centrifuged at 500 g for 10 min at 4° C. The supernatant is discarded and 20× the volume of the pellet of hypotonic buffer is added and the cells are carefully resuspended and incubated on ice for an hour. The cells are then physically lysed using procedures well-known in the art. Briefly, 5 ml of the cell suspension is placed in a glass Dounce homogenizer and homogenized with 20 strokes. Cell lysis is monitored microscopically to observe the point where isolated and yet undamaged nuclei result. Sucrose is added to make a final concentration of 250 mM sucrose (⅛ volume of 2 M stock solution in hypotonic buffer). The solution is carefully mixed by gentle inversion and then centrifuged at 400 g at 4° C. for 30 minutes. The supernatant is discarded and the nuclei are then gently resuspended in 20 volumes of nuclear buffer (10 mM HEPES, pH 7.5, 2 mM $MgCl_2$, 250 mM sucrose, 25 mM KCl, 1 mM DTT, 10 μM aprotinin, 10 μM leupeptin, 10 μM pepstatin A, 10 μM soybean trypsin inhibitor, and 100 μM PMSF). The nuclei are re-centrifuged as above and resuspended in 2× the volume of the pellet in nuclear buffer. The resulting nuclei may then be used directly in nuclear remodeling as described below or cryopreserved for future use.

Preparation of Condensation Extract

The condensation extract, when added to the isolated differentiated cell nuclei, will result in nuclear envelope breakdown and the condensation of chromatin. Since the purpose of step 1 is to remodel the nuclear components of a somatic differentiated cell with that of an undifferentiated cell, the condensation extract used in this example is obtained from NTera-2 cells which are also the cells used to derive the extract for nuclear envelope reconstitution above. This results in a dilution of the components from the differentiated cell in extracts which contain the corresponding components desirable in reprogramming cells to an undifferentiated state. NTera-2 cl. D1 cells are easily obtained from sources such as the American Type Culture Collection (CRL-1973) and are grown at 37° C. in monolayer culture in DMEM with 4 mM L-glutamine, 1.5 g/L sodium bicarbonate and 4.5 g/L glucose, 10% fetal bovine serum (complete medium). While in a log growth state, the cells are plated at $5 \times 10^6$ cells per sq cm tissue culture flask in 200 mL of complete medium. Methods of obtaining extracts capable of inducing nuclear envelope breakdown and chromosome condensation are well known in the art (Collas et al., J. Cell Biol. 147:1167-1180, (1999)). Briefly, NTera-2 cells in log growth as described above are synchronized in mitosis by incubation in 1 μg/ml nocodazole for 20 hours. The cells that are in the mitotic phase of the cell cycle are detached by mitotic shakeoff. The harvested detached cells are centrifuged at 500 g for 10 minutes at 4° C. Cells are resuspended in 50 ml of cold PBS, and centrifuged at 500 g for an additional 10 min. at 4° C. This PBS washing step is repeated once more. The cell pellet is then resuspended in 20 volumes of ice-cold cell lysis buffer (20 mM HEPES, pH 8.2, 5 mM $MgCl_2$, 10 mM EDTA, 1 mM DTT, 10 μM aprotinin, 10 μM leupeptin, 10 μM pepstatin A, 10 μM soybean trypsin inhibitor, 100 μM PMSF, and 20 μg/ml cytochalasin B, and the cells are centrifuged at 800 g for 10 minutes at 4° C. The supernatant is discarded, and the cell pellet is carefully resuspended in one volume of cell lysis buffer. The cells are placed on ice for one hour then lysed with a Dounce homogenizer. Progress is monitored by microscopic analysis until over 90% of cells and cell nuclei are lysed. The resulting lysate is centrifuged at 15,000 g for 15 minutes at 4° C., the tubes are then removed and immediately placed on ice. The supernatant is gently removed using a small caliber pipette tip, and the supernatant from several tubes is pooled on ice. If not used immediately, the extracts are immediately flash-frozen on liquid nitrogen and stored at −80EC until use. The cell extract is then placed in an ultracentrifuge tube and centrifuged at 200,000 g for three hours at 4° C. to sediment nuclear membrane vesicles. The supernatant is then gently removed and placed in a tube on ice and used immediately to prepare condensed chromatin or cryopreserved as described above.

Methods of Use of Condensation Extract

If beginning with a frozen aliquot on condensation extract, the frozen extract is thawed on ice. Then an ATP-generating system is added to the extract such that the final concentrations are 1 mM ATP, 10 mM creatine phosphate, and 25 µg/ml creatine kinase. The nuclei isolated from the differentiated cells as described above are then added to the extract at 2,000 nuclei per 10 µl of extract, mixed gently, the incubated in a 37° C. water bath. The tube is removed occasionally to gently resuspend the cells tapping on the tube. Extracts and cell sources vary in times for nuclear envelope breakdown and chromosome condensation. The progress is therefore monitored by periodic' monitoring samples microscopically. When the majority of cells have lost their nuclear envelope and there is evidence of the beginning of chromosome condensation, the extract containing the condensing chromosome masses is placed in a centrifuge tube with an equal volume of 1 M sucrose solution in nuclear buffer. The chromatin masses are sedimented by centrifugation at 1,000 g for 20 minutes at 4° C. The supernatant is discarded, and the chromatin masses are gently resuspended in nuclear remodeling extract derived above. The sample is then incubated in a water bath at 33° C. for up to two hours and periodically monitored microscopically for formation of remodeled nuclear envelopes around the condensed and remodeled chromatin as described (Burke & Gerace, Cell 44:639-652, (1986). Once a large percentage of chromatin has been encapsulated in nuclear envelopes, the remodeled nuclei may be used in cellular reconstitution using any of the techniques described in the present invention.

Modification of Cell Extracts

As an optional modification to the methods disclosed herein, one or more factors are expressed or overexpressed in the undifferentiated cells (for example, in EC or other cells) used to obtain the nuclear remodeling and/or condensation extracts. Such factors include, for example, SOX2, NANOG, cMYC, OCT4, DNMT3B, embryonic histones, as well as other factors listed in Table 1 below and regulatory RNA that induce or increase the expression of proteins expressed in undifferentiated cells and that improve the frequency of reprogramming. Any combinations of the above-mentioned factors may be used. For example, undifferentiated cells of the present invention may be modified to have increased expression of two, three, four, or more of any of the factors listed in Table 1. Alternatively, the level of one or more factors in the undifferentiated cells used to obtain the nuclear remodeling extract may be decreased relative to the levels found in unmodified cells. Such decreases in the level of a cell factor may be achieved by known methods, such as, for example, by use of transcriptional regulators, regulatory RNA, or antibodies specific for the cell factor.

Gene constructs encoding the proteins listed in Table 1 or their non-human homologues, or regulatory proteins or RNAs that alter expression of these factors, are transfected into the cells by standard techniques. Alternatively, recombinant proteins or other agents are directly added to the extracts.

Example 3

Genetic Modification of Remodeled Nuclei or Chromatin

The isolated nuclei or condensed chromatin may optionally be modified by methods involving recombinase treated targeting vectors or oligonucleotides. The DNA from cell free chromosomes and chromatin can be genetically modified enzymatically with targeting vectors or oligonucleotides, using purified recombinases, purified DNA repair proteins, or protein or cell extract preparations comprising such proteins. The targeting DNAs may have tens of kilobasepairs to oligonucleotides of at least 50 basepairs of homology to the chromosomal target. Recombinase catalyzed recombination intermediates formed between target chromosomes and vector DNA can be enzymatically resolved in cell free extracts with other purified recombination or DNA repair proteins to produce genetically modified chromosomes. These modified chromosomes can be reintroduced into cells or used in the formation of nuclei in vitro prior to introduction into cells; modified condensed chromatin can be used in nuclear envelope reconstitution (see step 2 below). Recombinase treated vector or oligonucleotides can also be directly introduced into isolated nuclei by microinjection or by diffusion into permeabilized nuclei to allow in situ formation of recombination intermediates that can be resolved in vitro, upon nuclear transfer into intact cells, or upon fusion with recipient cells.

In this approach, enyzmatically active nucleoprotein filaments are first formed between targeting vector, or oligonucleotides, and recombinase proteins. Recombinase proteins are cellular proteins that catalyze the formation of heteroduplex recombination intermediates intracellularly and can form similar intermediates in cell free systems. Well studied, prototype recombinases are the RecA protein from *E. coli* and Rad51 protein from eukaryotic organisms. Recombinase proteins cooperatively bind single stranded DNA and actively catalyze the search for homologous DNA sequences on other target chromosomal DNAs. Heteroduplex structures may also be formed and resolved using cell free extracts from cells with recombinogenic phenotypes (e.g., DT40 extracts). In a second step, heteroduplex intermediates may be resolved in cell free extracts by treatment with purified recombination and DNA repair proteins to recombine the donor targeting vector DNA or oligonucleotide into the target chromosomal DNA (FIG. 2). Resolution may also be accomplished using cell free extracts from normal cells or extracts from cells with a recombinogenic phenotype. Finally, the nuclear membrane is reformed around modified chromosomes and the remaining unmodified cellular chromosomal complement for introduction into recipient cells or oocytes.

Several techniques are available that can be used in gene modification of the reprogrammed cell. One technique is the Cre-Lox targeting system. Cre recombinase has been used to efficiently delete hundreds of basepairs to megabasepairs of DNA in mammalian cells. The LoxP and FRT recombinase recognition sequences allow recombinase mediated gene modifications of homologous recombinant cells.

Forming Recombinase Coated Nucleoprotein Filaments

Circular DNA targeting vectors are first linearized by treatment with restriction endonucleases, or alternatively linear DNA molecules are produced by PCR from genomic DNA or vector DNA. All DNA targeting vectors and traditional DNA constructs are removed from vector sequences by agarose gel electrophoresis and purified with Elutip-D columns (Schleicher & Schuell, Keene, N.H.). For RecA protein coating of DNA, linear, double-stranded DNA (200 ng) is heat denatured at 98° C. for 5 minutes, cooled on ice for 1 minute and added to protein coating mix containing Tris-acetate buffer, 2 mM magnesium acetate and 2.4 mM ATPγS. RecA protein (8.4 µg) is immediately added, the reaction incubated at 37° C. for 15 minutes, and magnesium acetate concentration increased to a final concentration of 11 mM. The RecA protein coating of DNA is monitored by agarose gel electrophoresis with uncoated double-stranded DNA as control. The electrophoretic mobility of RecA-DNA is significantly retarded as compared with non-coated double stranded DNA.

Isolation of cell free chromosomes and chromatin is achieved as described above. The condensation extract, when added to the isolated differentiated cell nuclei, will result in nuclear envelope breakdown and the condensation of chromatin. The resulting nuclei may then be used directly for gene modifications as just described, nuclear remodeling, or cryopreserved for future use. A separate extract is used for nuclear envelope reconstitution after cell free homologous recombination reactions have modified target chromosomes. Extract for nuclear envelope breakdown and chromatin condensation, and for nuclear envelope reconstitution may be prepared from any proficient mammalian cell line. However, extracts from the human embryonal carcinoma cell line NTera-2 can be potentially used for the condensation extract and for nuclear envelope reconstitution extract as well as for remodeling differentiated chromatin to an undifferentiated state, thus enhancing production of genetically modified human ES cells starting from differentiated human dermal cells.

Forming Heteroduplex Recombination Intermediates Between Preformed Recombinase Coated Nucleoprotein Targeting Vectors and Oligonucleotides and Cell Free Chromosomes and Chromatin Formation of targeting vector/chromosome heteroduplexes is performed by adding approximately 1-3 μg of double-stranded chromosomal DNA or chromatin masses to the RecA coated nucleoprotein filaments described above, and incubated at 37° C. for 20 minutes. If the nucleoprotein heteroduplex structures are to be deproteinized prior to additional in vitro recombination steps, they are treated by with the addition of SDS to a final concentration of 1.2%, or by addition of proteinase K to 10 mg/ml with incubation for 15 to 20 minutes at 37° C., followed by addition of SDS to a final concentration of 0.5 to 1.2% (wt/vol). Residual SDS is removed prior to subsequent steps by microdialysis against 100 to 1000 volumes of protein coating mix.

Resolving Recombination Intermediates with Cell Free Extracts

Cell free extracts may be prepared from normal fibroblast or hES cell lines, or may be prepared from cells demonstrated to have recombinogenic phenotypes. Cell lines exhibiting high levels of recombination in vivo are the chicken pre-B cell line DT40 and the human lymphoid DG75 cell line. Preparation of cell free extracts is performed at 4° C. About 108 actively growing cells are harvested from either dishes or suspension cultures. The cells are washed three times with phosphate-buffered saline (PBS; 140 mM NaCl, 3 mM KCl, 8 mM NaH$_2$PO$_4$, 1 mM K$_2$HPO$_4$, 1 mM MgCl$_2$, 1 mM CaCl$_2$), resuspended in 2 to 3 ml of hypotonic buffer A (10 mM Tris hydrochloride [pH 7.4], 10 mM MgCl$_2$, 10 mM KCl, 1 mM dithiothreitol), and kept on ice for 10 to 15 minutes. Phenylmethylsulfonyl fluoride is added to a concentration of 1 mM, and the cells are broken by 5 to 10 strokes in a Dounce homogenizer, pestle B. The released nuclei are centrifuged at 2,600 rpm in a Beckman TJ-6 centrifuge for 8 min. The supernatant is removed carefully and stored in 10% glycerol-100 mM NaCl at −70° C. (cytoplasmic fraction). The nuclei are resuspended in 2 ml of buffer A containing 350 mM NaCl, and the following proteinase inhibitors are added: pepstatin to a concentration of 0.25 μg/ml, leupeptin to a concentration of 0.1 μg/ml, aprotinin to a concentration of 0.1 μg/ml, and phenylmethylsulfonyl fluoride to a concentration of 1 mM (all from Sigma Chemicals). After 1 h of incubation at 0° C., the extracted nuclei are centrifuged at 70,000 rpm in a Beckman TL-100/3 rotor at 2° C. The clear supernatant is adjusted to 10% glycerol, 10 mM β-mercaptoethanol and frozen immediately in liquid nitrogen prior to storage at −70° C. (fraction 1).

To resolve recombination intermediates in vitro, chromosomal heteroduplex intermediates are incubated with 3 to 5 μg of extract protein in a reaction mixture containing 60 mM NaCl, 2 mM 2-mercaptoethanol, 2 mM KCl, 12 mM Tris hydrochloride (pH 7.4), 1 mM ATP, 0.1 mM each deoxyribonucleoside triphosphate (dNTP), 2.5 mM creatine phosphate, 12 mM MgCl$_2$, 0.1 mM spermidine, 2% glycerol, and 0.2 mM dithiothreitol. After 30 minutes at 37° C., the reaction is stopped by the addition of EDTA to a concentration of 25 μM, sodium dodecyl sulfate (SDS) to a concentration of 0.5%, and 20 μg of proteinase K and incubated for 1 hour at 37° C. SDS is removed prior to subsequent steps by microdialysis. An equal volume of 1 M sucrose is added to the treated chromatin masses—and sedimented by centrifugation at 1,000×g for 20 minutes at 4° C.

Reforming Nuclear Envelopes Around Recombinant Chromosomes and Chromatin

The supernatant is discarded, and the chromatin masses are gently resuspended in nuclear remodeling extract described above. The sample is then incubated in a water bath at 33° C. for up to two hours and periodically monitored microscopically for the formation of remodeled nuclear envelopes around the condensed and remodeled chromatin as described (Burke & Gerace, Cell 44:639-652, (1986). Once a large percentage of chromatin has been encapsulated in nuclear envelopes, the remodeled nuclei may be used for cellular reconstitution using any of the techniques described in the present invention.

Detection of Cells Containing Genetically Modified Chromosomes

Reconstituted cells are grown for 7 to 14 days and screened for recombinants using PCR and Southern hybridization.

Example 4

Modification of Chromosomes and Chromatin in Isolated Nuclei with Targeting Vectors or Oligonucleotides to Engineer Cells Chromosomes and chromatin may be genetically modified in isolated nuclei from cells. In this approach, intact nuclei are isolated from growing cells, and reversibly permeabilized to allow diffusion of nucleoprotein targeting vectors and oligonucleotides into the nucleus interior. Heteroduplex intermediates formed between nucleoprotein targeting vectors and oligonucleotides and chromosomal DNA may be resolved by treatment with recombination proficient cell extracts, purified recombination and DNA repair proteins, or by cellular reconstitution with the nuclei into recombination proficient cells.

Isolation and Permeabilization of Nuclei

Preparation of synchronous populations of nuclei cell culture and synchronization are carried out as previously described (Leno et al., Cell 69:151-158 (1992)). Nuclei are prepared as described except that all incubations are carried out in HE buffer (50 mM Hepes-KOH, pH 7.4, 50 mM KCl, 5 mM MgCl$_2$, 1 mM EGTA, 1 mM DTT, 1 μg/ml aprotinin, pepstatin, leupeptin, chymostatin).

Nuclear Membrane Permeablization Streptolysin O (SLO)-prepared nuclei (Leno et al., Cell 69:151-158 (1992)) are incubated with 20 µg/ml lysolecithin (Sigma Immunochemicals) and 10/µg/ml cytochalasin B in HE at a concentration of ~1.5×10$^4$ nuclei/ml for 10 min at 23° C. with occasional gentle mixing. Reactions are stopped by the addition of 1% nuclease free BSA (Sigma Immunochemicals). Nuclei are gently pelleted by centrifugation in a RC5B rotor (Sorvall Instruments, Newton, Conn.) at 500 rpm for 5 min and then washed three times by dilution in 1 ml HE. Pelleted nuclei are recovered in a small volume of buffer and resuspended to ~1×10$^4$ nuclei/µl.

Forming Heteroduplex Recombination Intermediates Between Preformed Recombinase Coated Nucleoprotein Targeting Vectors and Oligonucleotides and Cell Free Chromosomes and Chromatin Formation of targeting vector/chromosome heteroduplexes is performed by adding approximately 1×10$^5$ to 1×10$^6$ permeabilized nuclei to the RecA coated nucleoprotein filaments described above, and incubated at 37° C. for 20 minutes.

Resolving Recombination Intermediates with Cell Free Extracts

Cell free extracts may be prepared from normal fibroblast or hES cell lines, or may be prepared from cells demonstrated to have recombinogenic phenotypes. Cell lines exhibiting high levels of recombination in vivo are the chicken pre-B cell line DT40 and the human lymphoid DG75 cell line. Preparation of cell free extracts are performed at 4° C. About 10$^8$ actively growing cells are harvested from either dishes or suspension cultures. The cells are washed three times with phosphate-buffered saline (PBS; 140 mM NaCl, 3 mM KCl, 8 mM NaH$_2$PO$_4$, 1 mM K$_2$HPO$_4$, 1 mM MgCl$_2$, 1 mM CaCl$_2$), resuspended in 2 to 3 ml of hypotonic buffer A (10 mM Tris hydrochloride [pH 7.4], 10 mM MgCl$_2$, 10 mM KCl, 1 mM dithiothreitol), and kept on ice for 10 to 15 minutes. Phenylmethylsulfonyl fluoride is added to 1 mM, and the cells are broken by 5 to 10 strokes in a Dounce homogenizer, pestle B. The released nuclei are centrifuged at 2,600 rpm in a Beckman TJ-6 centrifuge for 8 min. The supernatant is removed carefully and stored in 10% glycerol-100 mM NaCl at −70° C. (cytoplasmic fraction). The nuclei are resuspended in 2 ml of buffer A containing 350 mM NaCl, and the following proteinase inhibitors are added: pepstatin to 0.25 µg/ml, leupeptin to 0.1 µg/ml, aprotinin to 0.1 µg/ml, and phenylmethylsulfonyl fluoride to 1 mM (all from Sigma Chemicals). After 1 h of incubation at 0° C., the extracted nuclei are centrifuged at 70,000 rpm in a Beckman TL-100/3 rotor at 2° C. The clear supernatant is adjusted to 10% glycerol, 10 mM β-mercaptoethanol and frozen immediately in liquid nitrogen prior to storage at −70° C. (fraction 1).

To resolve recombination intermediates in permeabilized nuclei, nuclei containing chromosomal heteroduplex intermediates are incubated with 3 to 5 µg of extract protein in a reaction mixture containing 60 mM NaCl, 2 mM 3-mercaptoethanol, 2 mM KCl, 12 mM Tris hydrochloride (pH 7.4), 1 mM ATP, 0.1 mM each deoxyribonucleoside triphosphate (dNTP), 2.5 mM creatine phosphate, 12 mM MgCl$_2$, 0.1 mM spermidine, 2% glycerol, and 0.2 mM dithiothreitol. After 30 minutes at 37° C., the reaction is stopped.

Nuclear Envelope Repair
Preparation and Fractionation of Nuclear Repair Extract

Low-speed Xenopus egg extracts (LSS) 1 are prepared essentially according to the procedure described by Blow and Laskey Cell 21; 47:577-87 (1986)). Extraction buffer (50 mM Hepes-KOH, pH 7.4, 50 mM KCl, 5 mM MgCl$_2$) is thawed and supplemented with 1 mM DTT, 1 µg/ml leupeptin, pepstatin A, chymostatin, aprotinin, and 10 µg/ml cytochalasin B (Sigma Immunochemicals, St. Louis, Mo.) immediately before use. Extracts are supplemented with 2% glycerol and snap-frozen as 10-20 µl beads in liquid nitrogen or subjected to further fractionation. High speed supernatant (HSS) and membrane fractious are prepared from low-speed egg extract as described (Sheehan et al., J Cell Biol. 106: 1-12 (1988)). Membranous material, isolated by centrifugation of 1-2 ml of low-speed extract, is washed at least two times by dilution in 5 ml extraction buffer. Diluted membranes are centrifuged for 10 minutes at 10k rpm in an SW50 rotor (SW50; Beckman Instruments, Inc., Palo Alto, Calif.) to yield vesicle fraction 1. The supernatant is then centrifuged for a further 30 min at 30k rpm to yield vesicle fraction 2. Washed membranes are supplemented with 5% glycerol and snap-frozen in 5 µl beads in liquid nitrogen. Vesicle fractions 1 and 2 are mixed in equal proportions before use in nuclear membrane repair reactions.

Treatment for Nuclear Envelope Repair

Lysolecithin-permeabilized nuclei are repaired by incubation with membrane components prepared from Xenopus egg extracts. Nuclei at a concentration of approximately 5000/µl are mixed with an equal volume of pooled vesicular fractions 1 and 2 and supplemented with 1 mM GTP and ATP. 10-20 µl reactions are incubated at 23° C. for up to 90 min with occasional gentle mixing. Aliquots are taken at intervals and assayed for nuclear permeability.

Once a large percentage of chromatin is encapsulated in nuclear envelopes, the remodeled nuclei may be used for cellular reconstitution using any of the techniques described in the present invention.

Detection of Cells Containing Genetically Modified Chromosomes

Reconstituted cells are grown for 7 to 14 days and screened for recombinants using PCR and Southern hybridization.

Example 5

Modification of Isolated Chromosomes, Chromatin, and Nuclei Using Cell Free Extracts to Engineer Cells with Exogenous Genetic Material In this approach, targeting vectors or oligonucleotides and the target chromosomal DNA are directly treated with recombination proficient cell free extracts from cells with recombinogenic phenotypes such as the chicken pre-B cell line DT40 and the human lymphoid cell line DG75. These cell free extracts may be used on isolated chromosome and chromatin or on isolated permeabilized nuclei. Essentially, targeting vector/oligonucleotides are incubated with isolated chromosomes, chromatin, or nuclei and cell free recombination extract. The nuclear envelope is reconstituted around recombinant chromosomes or chromatin, or the nuclear envelope of recombinant, permeabilized, nuclei are repaired prior to cell reconstitution with the reconstituted or repaired nuclei.

Preparation of Cell Free Extracts

Cell free extracts from DT40 or DG75 cells are prepared as described above.

Preparation of Chromosomes, Chromatin, or Nuclei

Isolated chromosomes, chromatin, and permeabilized nuclei from fibroblasts, hES cell lines, or germ cell lines are as described above.

Recombination Between Targeting Vectors and Oligonucleotides, and Cell Free Chromosomes and Chromatin Using Cell Free Extracts from Recombinogenic Cells Circular DNA targeting vectors are first linearized by treatment with restriction endonucleases, or alternatively linear DNA molecules are produced by PCR from genomic DNA or vector DNA. All DNA targeting vectors and traditional DNA constructs are removed from vector sequences by agarose gel electrophoresis and purified with Elutip-D columns (Schleicher & Schuell, Keene, N.H.). Double-stranded DNA (200 ng) is heat denatured at 98° C. for 5 minutes, cooled on ice for 1 minute and added to approximately 1-3 µg of double-stranded chromosomal DNA or chromatin masses, or approximately $1 \times 10^6$ to $1 \times 10^6$ permeabilized nuclei, and 3 to 5 µg of extract protein in a reaction mixture containing 60 mM NaCl, 2 mM 3-mercaptoethanol, 2 mM KCl, 12 mM Tris hydrochloride (pH 7.4), 1 mM ATP, 0.1 mM each deoxyribonucleoside triphosphate (dNTP), 2.5 mM creatine phosphate, 12 mM $MgCl_2$, 0.1 mM spermidine, 2% glycerol, and 0.2 mM dithiothreitol. The reaction mixtures are incubated at 37° C. for at least 30 minutes are processed as describe above prior to reconstituting cellular envelopes or repairing permeabilized nuclei.

Reforming Nuclear Envelopes Around Recombinant Chromosomes and Chromatin

Nuclear envelopes are reconstituted around recombinant chromosomes and chromatin and reconstituted nuclei used for cellular reconstitution as describe above.

Nuclear Envelope Repair

Recombinant, permeabilized nuclei are repaired and repaired recombinant nuclei used for cellular reconstitution as described above.

Detection of Cells Containing Genetically Modified Chromosomes

Reconstituted cells are grown for 7 to 14 days and screened for recombinants using PCR and Southern hybridization.

Example 6

Modification of Chromosomes and Chromatin in Intact Cells with Recombinase Treated Targeting Vectors or Oligonucleotides to Engineer Cells with Exogenous Genetic Material In this approach, double stranded targeting vectors, targeting DNA fragments, or oligonucleotides are coated with bacterial or eukaryotic recombinase and introduced into mammalian cells or oocytes. The activated nucleoprotein filament forms heteroduplex recombination intermediates with the chromosomal target DNA that is subsequently resolved to a homologous recombinant structure by the cellular homologous recombination or DNA repair pathways. While the most direct delivery of nucleoprotein filaments is by direct nuclear/pronuclear microinjection, other delivery technologies can be used including electroporation, chemical transfection, and single cell electroporation.

To form human Rad51 nucleoprotein filaments, linear, double-stranded DNA (200 ng) is heat denatured at 98° C. for 5 minutes, cooled on ice for 1 minute and added to a protein coating mix containing 25 mM Tris acetate (pH 7.5), 100 µg/ml BSA, 1 mM DTT, 20 mM KCl (added with the protein stock), 1 mM ATP and 5 mM $CaCl_2$, or AMP-PNP and 5 mM $MgCl_2$. hRad51 protein (1 µM) is immediately added and the reaction incubated for 10 minutes at 37° C. The hRad51 protein coating of the DNA is monitored by agarose gel electrophoresis with uncoated double-stranded DNA as control. The electrophoretic mobility of hRad51-DNA nucleoprotein filament is significantly retarded as compared with non-coated double stranded DNA. hRad51-DNA nucleoprotein filaments are diluted to a concentration of 5 ng/µl and used for nuclear microinjection of human fibroblasts or somatic cells, or used for pronuclear microinjection of activated oocytes created by somatic cell nuclear transfer or in vitro fertilization.

Detection of Cells Containing Genetically Modified Chromosomes

Injected cells or oocytes are grown for 7 to 14 days and screened for recombinants using PCR and Southern hybridization.

Example 7

Cellular Reconstitution

Step 2, also referred to as "cellular reconstitution" in the present invention is carried out using nuclei or chromatin remodeled by any of the techniques described in the present invention, such as in Examples 1 and 2 above or combinations of the techniques described in Examples 1 and 2 as described more fully in the present invention. During cellular reconstitution in this example, the remodeled nuclei are fused with enucleated cytoplasts of hES cells as is known in the art (Do & Scholer, Stem Cells 22:941-949 (2004)). Briefly, the human ES Cell line H9 is cultured under standard conditions (Klimanskaya et al., Lancet 365: 4997 (1995)). The cytoplasmic volume of the cells is increased by adding 10 µM cytochalasin B for 20 hours prior to manipulation. Cytoplasts are prepared by centrifuging trypsinzed cells through a Ficoll density gradient using a stock solution of autoclaved 50% (wt/vol) Ficoll-400 solution in water. The stock Ficoll 400 solution is diluted in DMEM and with a final concentration of 10 µM cytochalasin B. The cells are centrifuged through a gradient of 30%, 25%, 22%, 18%, and 15% Ficoll-400 solution at 36° C. Layered on top is 0.5 mL of 12.5% Ficoll-400 solution with $10 \times 10^6$ ES cells. The cells are centrifuged at 40,000 rpm at 36° C. in an MLS-50 rotor for 30 minutes. The cytoplasts are collected from the 15% and 18% gradient regions marked on the tubes, rinsed in PBS, and mixed on a 1:1 ratio with remodeled nuclei from step one of the present invention or cryopreserved. Fusion of the cytoplasts with the nuclei is performed using polyethylene glycol (see Pontecorvo "Polyethylene Glycol (PEG) in the Production of Mammalian Somatic Cell Hybrids" Cytogenet Cell Genet. 16(1-5):399-400 (1976), briefly in 1 mL of prewarmed 50% polyethylene glycol 1500 (Roche) for one minute. 20 mL of DMEM was then added over a five minute period to slowly remove the polyethylene glycol. The cells were centrifuged once at 130 g for five minutes and then taken back up in 50 µL of ES cell culture medium and placed beneath a feeder layer of fibroblasts under conditions to promote the outgrowth of an ES cell colony.

Example 8

Cellular Reconstitution

Step 2, also referred to as "cellular reconstitution" in the present invention is also carried out using nuclei remodeled by any of the techniques described in the present invention, in this example as in Example 2 above and the cellular reconstitution step that follows. The nuclei are fused with anucleate cytoplasmic blebs of hES cells as is well known in the art (Wright & Hayflick, Exp. Cell Res. 96:113-121, (1975); & Wright & Hayflick, Proc. Natl. Acad. Sci., USA, 72:1812-1816, (1975). Briefly, the cytoplasmic volume of the hES cells is increased by adding 10 µM cytochalasin B for 20 hours prior to manipulation. The cells are trypsinized and replated on sterile 18 mm coverslips coated with mouse embryonic fibroblast feeder extracellular matrix as described (Klimanskaya et al., Lancet 365: 4997 (2005). The cells are plated at a density such that after an overnight incubation at 37° C. and one gentle wash with medium, the cells cover about 90% of the surface area of the coverslip. The coverslips are then placed face down in a centrifuge tube containing 8 mL of 10% Ficoll-400 solution and centrifuged at 20,000 g at 36° C. for 60 minutes. Remodeled nuclei resulting from step one of the present invention are then spread onto the coverslip with a density of at least that of the cytoplasts, preferable at least five times the density of the cytoplasts. Fusion of the cytoplasts with the nuclei is performed using polyethylene glycol (see Pontecorvo "Polyethylene Glycol (PEG) in the Production of Mammalian Somatic Cell Hybrids" Cytogenet Cell Genet. 16(1-5):399-400 (1976). Briefly, in 1 mL of prewarmed 50% polyethylene glycol 1500 (Roche) in culture medium is placed over the coverslip for one minute. 20 mL of culture medium is then added drip-wise over a five minute period to slowly remove the polyethylene glycol. The entire media is then aspirated and replaced with culture medium.

Example 9

Analysis of the Molecular Mechanisms of Reprogramming

The in vitro remodeling of somatic cell-derived DNA as described in example 2 of the present invention is utilized as a model of the reprogramming of a somatic cell and an assay useful in analyzing the molecular mechanisms of reprogramming. The protocol of example 2 is followed to the time immediately preceding that when extracts from mitotic NTera2 cells are added. Prior to the addition of mitotic NTera2 cell extract, purified lamin A protein from human skin fibroblasts is added in amounts corresponding to $10^{-6}$, $10^{-4}$, $10^{-3}$, $10^{-2}$, $10^{-1}$, 1x and 10x the concentration in human fibroblast mitotic cell extract. The lamin A reduces the extent of successful reprogramming following step 2 cellular reconstitution, and the use of this assay system determines the extent of lamin A interference in successful reprogramming.

Example 10

Reprogramming Factors

The frequency of obtaining reprogrammed cells may be improved by increasing the expression of undifferentiated cell factors in the undifferentiated cells or cell extracts of steps 1 and 2 of the present invention. These factors may be introduced into the extracts of step 1, or into the enucleated cytoplasts of step 2 using techniques well known in the art and described herein. The final concentration of said factor should be at least the concentration observed in cultures of human ES cells grown under standard conditions, or preferably 2-50-fold higher in concentration than that observed in said standard hES cell cultures. Table 1 provides a list of exemplary undifferentiated cell factors. The table provides the names and accession names for the human genes; however homologues found in other species may also be used:

TABLE 1

| Gene Name | Accession Number |
|---|---|
| BARX1 | NM_021570.2 |
| CROC4 | NM_006365.1 |
| DNMT3B | NM_175849.1 |
| H2AFX | NM_002105.1 |
| HHEX | NM_002729.2 |
| HIST1H2AB | NM_003513.2 |
| HIST1H4J | NM_021968.3 |
| HMGB2 | NM_002129.2 |
| hsa-miR-18a | MI0000072 |
| hsa-miR-18b | MI0001518 |
| hsa-miR-20b | MI0001519 |
| hsa-miR-96 | MI0000098 |
| hsa-miR-106a | MI0000113 |
| hsa-miR-107 | MI0000114 |
| hsa-miR-141 | MI0000457 |
| hsa-miR-183 | MI0000273 |
| hsa-miR-187 | MI0000274 |
| hsa-miR-203 | MI0000283 |
| hsa-miR-211 | MI0000287 |
| hsa-miR-217 | MI0000293 |
| hsa-miR-218-1 | MI0000294 |
| hsa-miR-218-2 | MI0000295 |
| hsa-miR-302a | MI0000738 |
| hsa-miR-302c | MI0000773 |
| hsa-miR-302d | MI0000774 |
| hsa-miR-330 | MI0000803 |
| hsa-miR-363 | MI0000764 |
| hsa-miR-367 | MI0000775 |
| hsa-miR-371 | MI0000779 |
| hsa-miR-372 | MI0000780 |
| hsa-miR-373 | MI0000781 |
| hsa-miR-496 | MI0003136 |
| hsa-miR-508 | MI0003195 |
| hsa-miR-512-3p | |
| hsa-miR-512-5p | |
| hsa-miR-515-3p | |
| hsa-miR-515-5p | |
| hsa-miR-516-5p | |
| hsa-miR-517 | |
| hsa-miR-517a | MI0003161 |
| hsa-miR-518b | MI0003156 |
| hsa-miR-518c | MI0003159 |
| hsa-miR-518e | MI0003169 |
| hsa-miR-519e | MI0003145 |
| hsa-miR-520a | MI0003149 |
| hsa-miR-520b | MI0003155 |
| hsa-miR-520e | MI0003143 |
| hsa-miR-520g | MI0003166 |
| hsa-miR-520h | MI0003175 |
| hsa-miR-523 | MI0003153 |
| hsa-miR-524 | MI0003160 |
| hsa-miR-525 | MI0003152 |
| hsa-miR-526a-1 | MI0003157 |
| hsa-miR-526a-2 | MI0003168 |
| LEFTB | NM_020997.2 |
| LHX1 | NM_005568.2 |
| LHX6 | NM_014368.2 |
| LIN28 | NM_024674.3 |
| MYBL2 | NM_002466.2 |
| MYC | NM_002467.2 |
| MYCN | NM_005378.3 |
| NANOG | NM_024865.1 |
| NFIX | NM_002501.1 |
| OCT3/4 (POU5F1) | NM_002701.2 |
| OCT6 (POU3F1) | NM_002699.2 |
| OTX2 | NM_172337.1 |
| PHC1 | NM_004426.1 |
| SALL4 | NM_020436.2 |
| SOX2 | NM_003106.2 |
| TERF1 | NM_003218.2 |
| TERT | NM_198254.1 |
| TGIF | NM_003244.2 |
| VENTX2 | NM_014468.2 |
| ZIC2 | NM_007129.2 |
| ZIC3 | NM_003413.2 |
| ZIC5 | NM_033132.2 |
| ZNF206 | NM_032805.1 |

Methods for expressing proteins or regulatory RNA that increases expression of these proteins within cells or means of introducing these factors into cellular extracts are well-known in the art and include a variety of techniques including without limitation:

Viral infection for stable and transient expression of proteins and regulatory RNAs, such viruses including without limitation: lentivirus bovine papilloma and other papilloma viruses, adenoviruses and adeno-associated viruses. In addition, the genes or RNAs may be introduced by transfection for transient and stable expression of proteins and regulatory RNAs through the use of plasmid vectors, mammalian artificial chromosomes BACS/PACS the direct addition of the proteins encoded in the listed genes, the miRNA or mRNA listed, using CaPO4 precipitate-mediated endocytosis, dendrimers, lipids, electroporation, microinjection, homologous recombination to modify the gene or its promoters or enhancers, chromosome-mediated gene transfer, cell fusion, microcell fusion, or the addition of cell extracts containing said useful factors, all of such techniques are well-known in the art and protocols for carrying out said techniques to administer said factors are readily available to researchers in the literature and Internet.

Example 11

Induction Beta Cell Differentiation from Reprogrammed Cells without the Generation of ES Cell Lines Peripheral blood nucleated cells are obtained from a patient in need of pancreatic beta cells. The cells are purified using flow cytometry to obtain monocytes using techniques well-known in the art. Nuclei from the monocytes are then prepared by placing the cells in hypotonic buffer and dounce homogenizing the cells as is described in the art. The isolated monocyte nuclei from the patient are then exposed to a mitotic extract from the human EC cell line Tera-2 and incubated while monitoring samples of the extract to observed nuclear envelope breakdown and subsequent reformation of the nuclear envelope as described herein. The resulting reprogrammed cell nuclei are then fused with EC cell cytoplasts from the EC cell line Tera-2 that have been transfected with plasmids to overexpress the genes OCT4, SOX2, and NANOG as described herein. The resulting reconstituted cells in a heterogeneous mixture of reprogrammed and non-reprogrammed cells are then permeabilized and exposed to extracts of beta cells isolated from bovine pancreas as described herein and then directly differentiated into endodermal lineages without the production of an ES cell line. One million of the heterogeneous mixture of cells are then added onto mitotically-inactivated feeder cells that express high levels of NODAL or cell lines that express members of the TGF beta family that activate the same receptor as NODAL such as CM02 cells that express relatively high levels of Activin-A, but low levels of Inhibins or follistatin. The cells are then incubated for a period of five days in DMEM medium with 0.5% human serum. After five days, the resulting cells which include definitive endodermal cells are purified by flow cytometry or other affinity-based cell separation techniques such as magnetic bead sorting using antibody specific to the CXCR4 receptor and then cloned using techniques described in the pending patent applications PCT/US2006/013573 filed Apr. 11, 2006; and U.S. Application No. 60/811,908, filed Jun. 7, 2006, which are incorporated by means of reference. These cells are then directly differentiated into pancreatic beta cells or beta cell precursors using techniques known in the art for differentiating said cells from human embryonic stem cell lines or by culturing the cells on inducer cell mesodermal cell lines as described in PCT/US2006/013573 filed Apr. 11, 2006, and U.S. Application No. 60/811,908, filed Jun. 7, 2006, which are both incorporated by means of reference.

It is envisioned that the disclosed improved methods for the reprogramming of animal somatic cells are generally useful in mammalian and human cell therapy, such as human cells useful in treating dermatological, cardiovascular, neurological, endocrinological, skeletal, and blood cell disorders.

From the foregoing description, it will be apparent that variations and modifications may be made to the invention described herein to adopt it to various usages and conditions.

What is claimed is:
1. A method comprising
   (a) contacting an isolated mammalian somatic cell or a nucleus thereof with a cell-free extract
      (i) obtained from undifferentiated cells engineered to overexpress one or more reprogramming factors and/or
      (ii) supplemented with one or more reprogramming factors,
   wherein the reprogramming factors are selected from the group consisting of BARX1, CROC4, DNMT3B, H2AFX, HHEX, HISTIH2AB, HISTIH4J, HMGB2, hsa-miR-18a, hsa-miR-18b, hsa-miR-20b, hsa-miR-96, hsa-miR-106a, hsa-miR-107, hsa-miR-141, hsa-miR-183, hsa-miR-187, hsa-miR-203, hsa-miR-211, hsa-miR-217, hsa-miR-218-1, hsa-miR-218-2, hsa-miR-302a, hsa-miR-302c, hsa-miR-302d, hsa-miR-330, hsa-miR-363, hsa-miR-367, hsa-miR-371, hsa-miR-372, hsa-miR-373, hsa-miR-496, hsa-miR-50B, hsa-miR-512-3p, hsa-miR-512-5p, hsa-miR-515-3p, hsa-miR-515-5p, hsa-miR-516-5p, hsa-miR-517, hsa-miR-517a, hsa-miR-518b, hsa-miR-51Bc, hsa-miR-518e, hsa-miR-51ge, hsa-miR-520a, hsa-miR-520b, hsa-miR-520e, hsa-miR-520g, hsa-miR-520h, hsa-miR-523, hsa-miR-524, hsa-miR-525, hsa-miR-526a-1, hsa-miR-526a-2, LEFTB, LHX1, LHX6, LIN28, MYBL2, MYC, MYCN, NANOG, NFIX, OCT3/4(POU5F1), OCT6 (POU3F1), OTX2, PHC1, SALL4, SOX2, TERF1, TERT, TGIF, VENTX2, ZIC2, ZIC3, ZICS, and ZNF206; and
   (b) analyzing the karyotype and/or the extent of reprogramming of the mammalian cell or nucleus thereof produced by step (a).
2. The method of claim 1, wherein step (b) comprises analyzing whether the mammalian cell displays a gene expression pattern expected of undifferentiated cells.
3. The method of claim 2, wherein the undifferentiated cells are embryonic stem cells.
4. The method of claim 1, wherein step (b) comprises karyotyping the mammalian somatic cell or nucleus thereof by chromosome spread, spectral karyotyping, telomere length assay, or total genomic hybridization assay.
5. The method of claim 1, wherein step (b) comprises determining whether the mammalian cell or nucleus thereof expresses
   (1) E-cadherin mRNA at levels of at least 5% of the expression level of the housekeeping gene GAPD; and/or
   (2) detectable telomerase reverse transcriptase mRNA or telomerase activity as assessed by the Telomeric Repeat Amplification Protocol (TRAP) assay; and/or

(3) LIN28 expression at levels of at least 5% of the housekeeping gene GAPD.

6. The method of claim 1, wherein the reprogramming factors are selected from the group consisting of SOX2, NANOG, MYC, OCT3/4, and DNMT3B.

7. The method of claim 1, wherein the reprogramming factors are proteins.

8. The method of claim 1, wherein the reprogramming factors are microRNAs.

9. A method comprising
(a) contacting an isolated mammalian somatic cell or a nucleus thereof with a cell-free extract
   (i) obtained from undifferentiated cells engineered to overexpress one or more reprogramming factors and/or
   (ii) supplemented with one or more reprogramming factors,
wherein the reprogramming factors are selected from the group consisting of hsa-miR-18a, hsa-miR-18b, hsa-miR-20b, hsa-miR-96, hsa-miR-106a, hsa-miR-107, hsa-miR-141, hsa-miR-183, hsa-miR-187, hsa-miR-203, hsa-miR-211, hsa-miR-217, hsa-miR-218-1, hsa-miR-218-2, hsa-miR-302a, hsa-miR-302c, hsa-miR-302d, hsa-miR-330, hsa-miR-363, hsa-miR-367, hsa-miR-371, hsa-miR-372, hsa-miR-373, hsa-miR-496, hsa-miR-50B, hsa-miR-512-3p, hsa-miR-512-5p, hsa-miR-515-3p, hsa-miR-515-5p, hsa-miR-516-5p, hsa-miR-517, hsa-miR-517a, hsa-miR-518b, hsa-miR-51Bc, hsa-miR-518e, hsa-miR-51ge, hsa-miR-520a, hsa-miR-520b, hsa-miR-520e, hsa-miR-520g, hsa-miR-520h, hsa-miR-523, hsa-miR-524, hsa-miR-525, hsa-miR-526a-1, and hsa-miR-526a-2; and
(b) analyzing the karyotype and/or the extent of reprogramming of the mammalian cell or nucleus thereof produced by step(a) by
   (i) karyotyping the mammalian cell or nucleus thereof by chromosome spread, spectral karyotyping, or total genomic hybridization assay, or
   (ii) determining whether the cell or nucleus thereof expresses
      (1) E-cadherin mRNA at levels of at least 5% of the expression level of the housekeeping gene GAPD; and/or
      (2) LIN28expression at levels of at least 5% of the housekeeping gene GAPD.

10. A method comprising
(a) contacting an isolated mammalian somatic cell or a nucleus thereof with a cell-free extract,
   (i) from human embryonic stem cells, engineered to overexpress one or more reprogramming factors and/or
   (ii) supplemented with one or more reprogramming factors,
wherein the reprogramming factors are selected from the group consisting of BARX1, CROC4, DNMT3B, H2AFX, HHEX, HISTIH2AB, HISTIH4J, HMGB2, hsa-miR-18a, hsa-miR-18b, hsa-miR-20b, hsa-miR-96, hsa-miR-106a, hsa-miR-107, hsa-miR-141, hsa-miR-183, hsa-miR-187, hsa-miR-203, hsa-miR-211, hsa-miR-217, hsa-miR-218-1, hsa-miR-218-2, hsa-miR-302a, hsa-miR-302c, hsa-miR-302d, hsa-miR-330, hsa-miR-363, hsa-miR-367, hsa-miR-371, hsa-miR-372, hsa-miR-373, hsa-miR-496, hsa-miR-50B, hsa-miR-512-3p, hsa-miR-512-5p, hsa-miR-515-3p, hsa-miR-515-5p, hsa-miR-516-5p, hsa-miR-517, hsa-miR-517a, hsa-miR-518b, hsa-miR-51Bc, hsa-miR-518e, hsa-miR-51ge, hsa-miR-520a, hsa-miR-520b, hsa-miR-520e, hsa-miR-520g, hsa-miR-520h, hsa-miR-523, hsa-miR-524, hsa-miR-525, hsa-miR-526a-1, hsa-miR-526a-2, LEFTB, LHX1, LHX6, LIN28, MYBL2, MYC, MYCN, NANOG, NFIX, OCT3/4(POU5F1), OCT6 (POU3F1), OTX2, PHC1, SALL4, SOX2, TERF1, TERT, TGIF, VENTX2, ZIC2, ZIC3, ZIC5, and ZNF206; and
(b) analyzing the karyotype and/or the extent of reprogramming of the mammalian cell or nucleus thereof produced by step (a) by
   (i) karyotyping the mammalian cell or nucleus thereof by chromosome spread, spectral karyotyping, or total genomic hybridization assay, or
   (ii) determining whether the cell or nucleus thereof expresses
      (1) E-cadherin mRNA at levels of at least 5% of the expression level of the housekeeping gene GAPD; and/or
      (2) LIN28 expression at levels of at least 5% of the housekeeping gene GAPD.

* * * * *

UNITED STATES PATENT AND TRADEMARK OFFICE
CERTIFICATE OF CORRECTION

PATENT NO. : 10,501,723 B2
APPLICATION NO. : 14/525378
DATED : December 10, 2019
INVENTOR(S) : Michael D. West et al.

It is certified that error appears in the above-identified patent and that said Letters Patent is hereby corrected as shown below:

In the Claims

In Claim 1, at Column 40, Line 45, "ZICS" should read "ZIC5".

In Claim 9, at Column 41, Line 44, "LIN28expression" should read "LIN28 expression".

Signed and Sealed this
Seventeenth Day of March, 2020

Andrei Iancu
*Director of the United States Patent and Trademark Office*